US012638449B2

(12) United States Patent
Wang et al.

(10) Patent No.: US 12,638,449 B2
(45) Date of Patent: May 26, 2026

(54) METHODS AND RELATED ASPECTS FOR DETECTING UNLABELED BIOMOLECULES

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Guangzhong Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 575 days.

(21) Appl. No.: 18/319,157

(22) Filed: May 17, 2023

(65) Prior Publication Data

US 2023/0384311 A1 Nov. 30, 2023

Related U.S. Application Data

(60) Provisional application No. 63/345,962, filed on May 26, 2022.

(51) Int. Cl.
G01N 33/543 (2006.01)
G01N 33/573 (2006.01)

(52) U.S. Cl.
CPC ..... G01N 33/573 (2013.01); G01N 33/54386 (2013.01); *G01N 2333/912* (2013.01)

(58) Field of Classification Search
CPC .......... G01N 33/573; G01N 33/54386; G01N 2333/912; G01N 2021/5903; G01N 2021/258; G01N 21/553; G01N 21/554; G01N 21/648; G01N 33/48; G01N 33/5005; G01N 33/5302; G01N 33/5304;
(Continued)

(56) References Cited

U.S. PATENT DOCUMENTS 12,306,098 B2 * 5/2025 Wang ..................... G01N 21/51

OTHER PUBLICATIONS

Zhang et al. Quantification of Single-Molecule Protein Binding Kinetics in Complex Media with Prism-Coupled Plasmonic Scattering Imaging. ACS Sens. Mar. 26, 2021;6(3):1357-1366. Epub Mar. 15, 2021. (Year: 2021).*

(Continued)

*Primary Examiner* — Christopher L Chin
*Assistant Examiner* — Ellis Follett Lusi
(74) *Attorney, Agent, or Firm* — MH2 Technology Law Group LLP

(57) ABSTRACT

Provided herein are methods of detecting unlabeled biomolecules. In some embodiments, the methods include disrupting a cell population sufficient to release unlabeled biomolecules from the cell population to produce released biomolecules in which the cell population is disposed on a first inner surface of a chamber that is disposed substantially within a fluidic device and in which the chamber comprises a fluidic material. In some embodiments, the methods also include binding the released biomolecules to a second inner surface of the chamber to produce surface-bound biomolecules, introducing an incident light toward the second inner surface of the chamber concurrent with, and/or after, producing the surface-bound biomolecules, and detecting light scattered by the surface-bound biomolecules over a duration to produce a set of biomolecule imaging data. Related fluidic devices, systems, and computer readable media are also provided.

26 Claims, 21 Drawing Sheets

(58) Field of Classification Search
CPC ............. G01N 33/543; G01N 33/6803; G01N
33/6863; G01N 21/01; G01N 21/05;
G01N 21/17; B01L 2200/027; B01L
9/527; B01L 3/5027
USPC ... 435/7.1, 7.21, 287.2, 287.3, 288.3, 288.5;
422/502, 509; 436/501, 518, 524
See application file for complete search history.

(56) References Cited

OTHER PUBLICATIONS

Wang et al. Toward Single-Cell Single-Molecule Pull-Down. Biophys
J. Jul. 17, 2018;115(2):283-288. Epub May 25, 2018. (Year: 2018).*

* cited by examiner

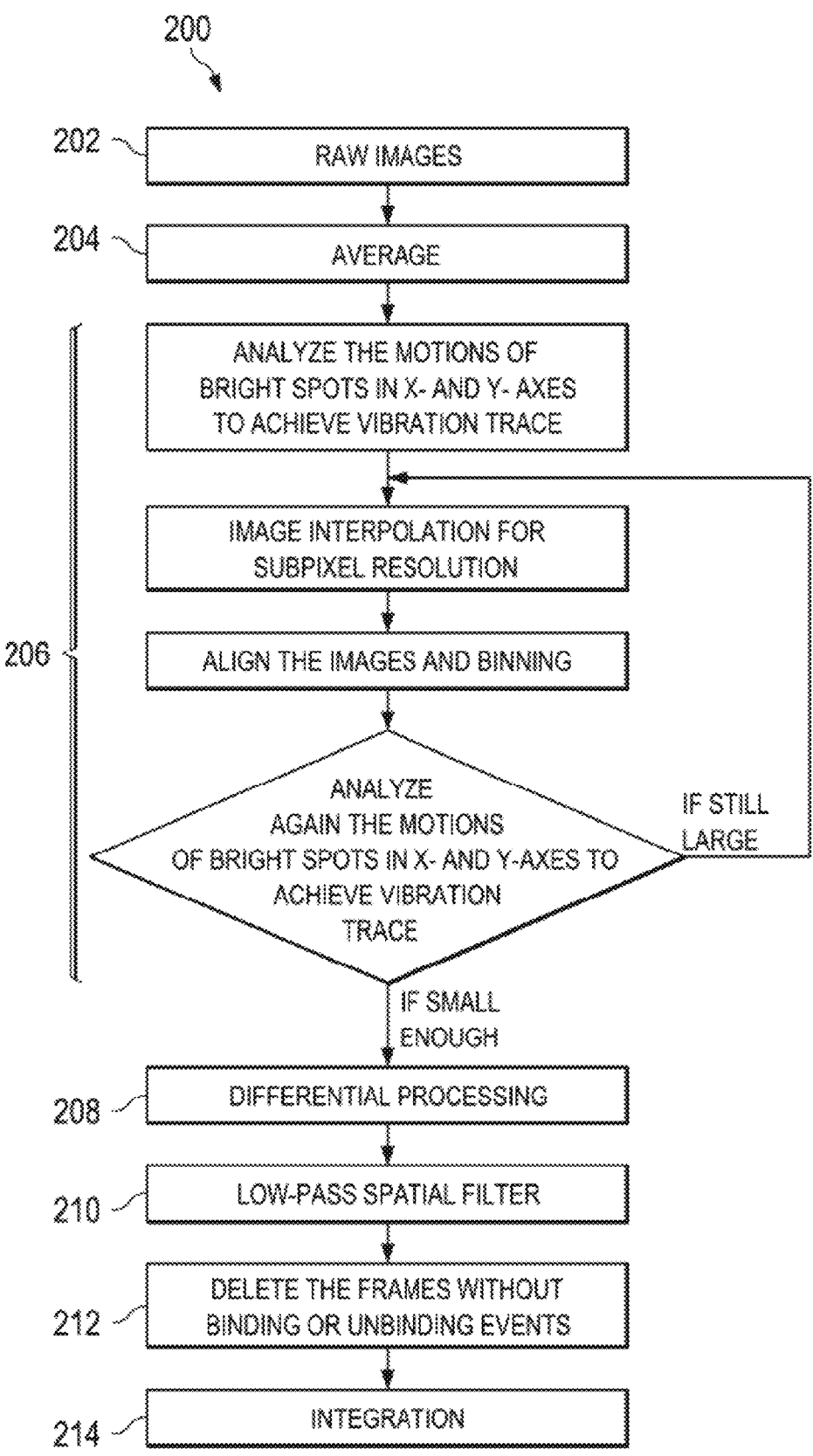

200

202 RAW IMAGES

204 AVERAGE

206 ANALYZE THE MOTIONS OF BRIGHT SPOTS IN X- AND Y- AXES TO ACHIEVE VIBRATION TRACE

IMAGE INTERPOLATION FOR SUBPIXEL RESOLUTION

ALIGN THE IMAGES AND BINNING

ANALYZE AGAIN THE MOTIONS OF BRIGHT SPOTS IN X- AND Y-AXES TO ACHIEVE VIBRATION TRACE

IF STILL LARGE

IF SMALL ENOUGH

208 DIFFERENTIAL PROCESSING

210 LOW-PASS SPATIAL FILTER

212 DELETE THE FRAMES WITHOUT BINDING OR UNBINDING EVENTS

214 INTEGRATION

FIG. 2

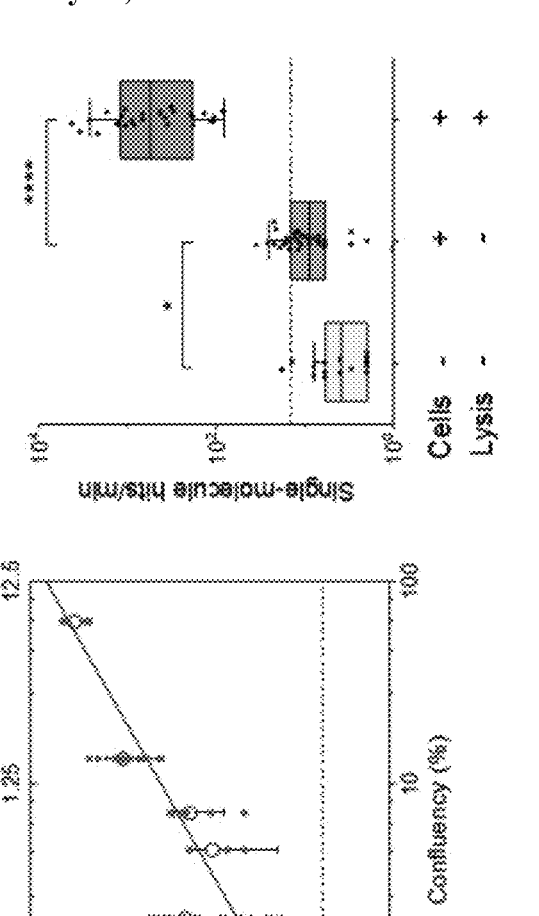
FIG. 3I
FIG. 3H
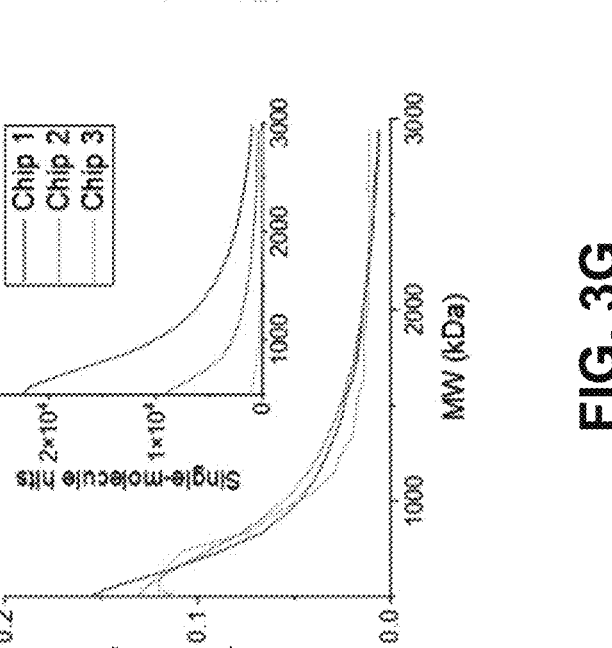
FIG. 3G

Protein complex        Denatured proteins

METHODS AND RELATED ASPECTS FOR DETECTING UNLABELED BIOMOLECULES

CROSS-REFERENCE TO RELATED APPLICATIONS

This application claims the benefit of U.S. Provisional Patent Application Ser. No. 63/345,962, filed May 26, 2022, the disclosure of which is incorporated herein by reference.

BACKGROUND

In cells, proteins transduce signals and carry out their functions via phosphorylation and assembly into protein complexes. Hence, measuring the abundance and composition of intracellular proteins involved in the pathway has been the most direct way to study these processes and the underlying molecular mechanisms. This task is often accomplished by polyacrylamide gel electrophoresis (PAGE) and western blot, which separate the proteins and probe the protein of interest using antibodies. Nevertheless, conventional PAGE and western blot require a substantial number of cells (at least thousands) to reach sufficient signal-to-noise ratio, which limits the detection of rare cells or low-abundant proteins. Recently, a technique called single-cell western-blot (scWB) has been developed to probe proteins with single cell resolution. Although scWB has improved detection sensitivity, it denatures protein complexes (like the traditional SDS-PAGE), making it difficult to interpret their native composition and function in cells.

To address these problems, single-molecule fluorescence techniques, such as single-molecule pull-down (SiMPull), single-molecule co-immunoprecipitation, and single-molecule fluorescence resonance energy transfer (FRET) have emerged as sensitive and non-destructive tools for measuring intracellular protein complexes and their composition. However, apart from time-consuming, the genetically encoded or chemically attached fluorescent tags may introduce complication by interacting with off-target proteins or altering the interaction affinity. In addition, fluorescence is not applicable for long-term and continuous imaging due to photobleaching, which affects measuring the binding kinetics of proteins.

Accordingly, there is a need for additional techniques for detecting unlabeled biomolecules.

SUMMARY

This disclosure describes fluidic devices, systems, computer readable media, and methods for detecting unlabeled biomolecules. In some embodiments, for example, the methods and related aspects of the present disclosure directly and specifically image intact individual protein complexes immediately after being released from lysed cells, and are non-destructive compared with techniques, such as single-cell western blotting. The methods and related aspects of the present disclosure typically measure scattered light from single molecules that are not fluorescently labelling and hence, not susceptible to quenching. The measured scattered light intensity is proportional to the molecular weight, and accordingly, the methods disclosed herein provide additional information on the detected single molecules. In addition, the label-free feature of the present disclosure also allows for binding kinetics analysis, which can be used, for example, to distinguish specific binding and nonspecific binding. These and other attributes of the present disclosure will be apparent upon a complete review of the specification, including the accompanying figures.

In one aspect, the present disclosure provides a method of detecting unlabeled biomolecules. The method includes disrupting a cell population sufficient to release at least some unlabeled biomolecules from at least one cell in the cell population to produce released biomolecules, wherein the cell population is disposed on a first inner surface of a chamber that is disposed substantially within a fluidic device and wherein the chamber comprises a fluidic material. The method also includes binding at least a portion of the released biomolecules to a second inner surface of the chamber to produce one or more surface-bound biomolecules, introducing an incident light toward the second inner surface of the chamber concurrent with, and/or after, producing the surface-bound biomolecules, and detecting light scattered by the surface-bound biomolecules over a first duration to produce a set of biomolecule imaging data.

In some embodiments, the method further includes culturing the cell population on the first inner surface of the chamber prior to performing the disrupting step. In some embodiments, the method performing the disrupting, binding, introducing, and detecting steps substantially simultaneously with one another. In some embodiments, the method is less destructive to the released biomolecules when compared to a western blotting technique that uses an identical cell population. In some embodiments, the method includes detecting the light scattered by the surface-bound biomolecules in substantially real-time. In some embodiments, the detecting step comprises detecting evanescent light scattered by individual surface-bound biomolecules. In some embodiments, the cell population comprises one or more cells, 10 or more cells, 100 or more cells, 1000 or more cells, 10000 or more cells, 100000 or more cells, or 1000000 or more cells. In some embodiments, the unlabeled biomolecules comprise proteins and/or protein complexes. In some embodiments, the unlabeled biomolecules comprise nucleic acids. In some embodiments, at least some of the unlabeled biomolecules are released from within the at least one cell in the cell population. In some embodiments, the set of biomolecule imaging data comprises video data.

In some embodiments, the method further comprises determining a composition of at least one of the unlabeled biomolecules using the set of biomolecule imaging data. In some embodiments, the method further comprises quantifying the unlabeled biomolecules and/or binding kinetics thereof using the set of biomolecule imaging data. In some embodiments, the method includes introducing the incident light toward the second inner surface via a second outer surface of the chamber.

In some embodiments, disrupting the cell population comprises lysing the at least one cell in the cell population. In some embodiments, the at least one cell in the cell population is lysed using at least one laser. In some embodiments, the fluidic material comprises at least one chemical lysing agent and wherein at least one cell in the cell population is lysed using the at least one chemical lysing agent.

In some embodiments, the fluidic device comprises at least one inlet port and at least one outlet port that both fluidly communicate with the chamber and wherein the method further comprises flowing the fluidic material into the chamber via the inlet port and out of the chamber via outlet port. In some embodiments, the fluidic material comprises a ligand that binds to the surface-bound biomolecules to produce one or more surface-bound ligand-biomolecule complexes and wherein the method further comprises detecting light scattered by the surface-bound ligand-biomolecule complexes over a second duration to produce a set of ligand-biomolecule complex imaging data. In some embodiments, the ligand comprises a protein or a nucleic acid. In some embodiments, the first duration and the second duration are identical to one another. In some embodiments, the method further comprises detecting size or volume changes of the surface-bound ligand-biomolecule complexes during at least a portion of the second duration from the set of ligand-biomolecule complex imaging data to thereby determine a molecular binding kinetics measure of the unlabeled biomolecules. In some embodiments, the method includes quantifying an amount of interaction between the surface-bound biomolecules and the ligand.

In some embodiments, the second surface of the chamber comprises a plurality of biomolecule capture moieties that are capable of binding the released biomolecules and wherein the method comprises binding the released biomolecules to the second surface of the chamber via at least a portion of the plurality of biomolecule capture moieties to produce the one or more surface-bound biomolecules. In some embodiments, the biomolecule capture moieties are selected from the group consisting of: antibodies, aptamers, and receptors. In some embodiments, the method further comprises distinguishing between specific and nonspecific binding to the plurality of biomolecule capture moieties using the set of biomolecule imaging data.

In some embodiments, the second inner surface is coated with a metallic layer and wherein an incident angle of the incident light is selected to create surface plasmon resonance on the metallic layer. In some embodiments, the metallic layer comprises gold (Au).

In some embodiments, a roughness of the second inner surface is selected such that light scattered by the second inner surface interferes with at least some of the light scattered by the surface-bound biomolecules. In some embodiments, the method further comprises counting a number of individual surface-bound biomolecules over the first duration to produce a count and fitting the count with a binding model to determine kinetic constants and/or at least one affinity value. In some embodiments, the first and/or second duration comprises about 15 minutes, about 10 minutes, about 5 minutes, or less time.

In another aspect, the present disclosure provides a fluidic device that includes a body structure that defines at least one chamber disposed substantially within the body structure, wherein the chamber comprises a fluidic material and at least first and second inner surfaces, wherein a cell population is disposed on the first inner surface, and wherein the second inner surface is coated with a metallic layer that is configured to create surface plasmon resonance when incident light is introduced toward the second inner surface at a suitable incident angle via a second outer surface of the chamber. In some embodiments, the fluidic device further comprises at least one inlet port and at least one outlet port that both fluidly communicate with the chamber. In some embodiments, the metallic layer comprises gold (Au). In some embodiments, the second surface comprises a plurality of biomolecule capture moieties that are capable of binding unlabeled biomolecules when the unlabeled biomolecules are released from at least one cell in the cell population. In some embodiments, the biomolecule capture moieties are selected from the group consisting of: antibodies, aptamers, protein, glycan and nucleic acid receptors.

In another aspect, the present disclosure provides a system for detecting unlabeled biomolecules. The system includes a fluidic device receiving area configured to receive a fluidic device that comprises a body structure that defines at least one chamber disposed substantially within the body structure, wherein the chamber comprises a fluidic material and at least first and second inner surfaces, wherein a cell population is disposed on the first inner surface, and wherein the second inner surface is coated with a metallic layer that is configured to create surface plasmon resonance when incident light is introduced toward the second inner surface at a suitable incident angle via a second outer surface of the chamber. The system also includes a light source configured to introduce an incident light toward the fluidic device receiving area, and a detector configured to collect light scattered by surface-bound biomolecules when the fluidic device is received in the fluidic device receiving area and the incident light is introduced from the light source. In addition, the system also includes a controller that comprises, or is capable of accessing, computer readable media comprising non-transitory computer-executable instructions which, when executed by at least one electronic processor, perform at least: disrupting the cell population sufficient to release at least some unlabeled biomolecules from at least one cell in the cell population to produce released biomolecules such that at least a portion of the released biomolecules bind to the second inner surface of the chamber to produce one or more surface-bound biomolecules when the fluidic device is received in the fluidic device receiving area; introducing the incident light from the light source at the suitable incident angle toward the second inner surface of the chamber when the fluidic device is received in the fluidic device receiving area; and detecting light scattered by the surface-bound biomolecules over a duration to produce a set of biomolecule imaging data to thereby detect the unlabeled biomolecules using the detector when the fluidic device is received in the fluidic device receiving area.

In another aspect, the present disclosure provides a computer readable media comprising non-transitory computer executable instructions which, when executed by at least one electronic processor, perform at least: disrupting a cell population sufficient to release at least some unlabeled biomolecules from at least one cell in the cell population to produce released biomolecules, wherein the cell population is disposed on a first inner surface of a chamber that is disposed substantially within a fluidic device and wherein the chamber comprises a fluidic material, such that at least a portion of the released biomolecules bind to a second inner surface of the chamber to produce one or more surface-bound biomolecules; introducing an incident light from a light source toward the second inner surface of the chamber; and detecting light scattered by the surface-bound biomolecules over a duration to produce a set of biomolecule imaging data to thereby detect the unlabeled biomolecules using a detector. In some embodiments of the systems and computer readable media disclosed herein, the set of biomolecule imaging data comprises video data. In some embodiments of the systems and computer readable media disclosed herein, the duration comprises about 15 minutes, about 10 minutes, about 5 minutes, or less time.

In some embodiments of the systems and computer readable media disclosed herein, the non-transitory computer-executable instructions which, when executed by the electronic processor, further perform at least: determining a molecular weight of at least one of the unlabeled biomolecules using the set of biomolecule imaging data. In some embodiments of the systems and computer readable media disclosed herein, the non-transitory computer-executable instructions which, when executed by the electronic processor, further perform at least: determining a composition of at least one of the unlabeled biomolecules using the set of biomolecule imaging data. In some embodiments of the systems and computer readable media disclosed herein, the non-transitory computer-executable instructions which, when executed by the electronic processor, further perform at least: quantifying the unlabeled biomolecules and/or binding kinetics thereof using the set of biomolecule imaging data. In some embodiments of the systems and computer readable media disclosed herein, the non-transitory computer-executable instructions which, when executed by the electronic processor, perform at least: disrupting the cell population using at least one laser. In some embodiments of the systems and computer readable media disclosed herein, the fluidic device comprises at least one inlet port and at least one outlet port that both fluidly communicate with the chamber and wherein the non-transitory computer-executable instructions which, when executed by the electronic processor, further perform at least: flowing the fluidic material into the chamber via the inlet port and out of the chamber via outlet port using at least one fluid conveyance device. In some embodiments of the systems and computer readable media disclosed herein, the second surface of the chamber comprises a plurality of biomolecule capture moieties that bind the released biomolecules to produce the one or more surface-bound biomolecules.

BRIEF DESCRIPTION OF DRAWINGS

FIG. 2 is a schematic diagram showing exemplary steps performed by an image processing algorithm that are suitable for use with certain aspects disclosed herein.

FIGS. 3A-3I. The principle of single-protein imaging and cell lysis detection. a, Experimental setup. Cells are cultured on the top glass surface of the flow chamber. After introducing lysis buffer, intracellular molecules are released and diffuse to the bottom gold film surface. An incident light is guided to the gold film by a prism to excite SPR on the surface. Single molecules hit the surface and scatter the light in the evanescent field, which is imaged by a CMOS camera via an objective above the chamber. b, The top surface imaged in bright field showing the morphology of a single cell before and after lysis. Scale bar, 15 μm. The bottom surface recorded in PSM mode shows the scattering of the surface. Single molecules are revealed after removing the background by differential imaging, where each bright spot indicated by the arrows is a single protein or complex molecule. Scale bar, 3 μm. c, The conversion from scattered light intensity to molecular weight (MW) is calibrated using protein samples in PBS solution. Error bars represent the mean±standard deviation (s.d.) obtained from >1000 single molecules. The blank sample is pure PBS solution, showing the system noise level. The dashed line marks the detection limit of the PSM imaging technique, defined by mean+3× s.d. of the blank. d, Temporal profile of the release of intracellular molecules during cell lysis. Lysis buffer was injected at t=0 and flowed at 50 μL/min in the chamber. Top panel: cumulative single-molecule hits on the surface. Bottom left panel: mass distribution of single molecules over time after the lysis, where each point is from a single molecule. Bottom right panel: MW histogram obtained by projecting the single molecule data. e, Temporal profile of single molecule hits without flow after cell lysis. The flow was stopped immediately after introducing lysis buffer. The cell confluence in d and e are 10% and 15%, respectively. f, Cumulative single molecule hits obtained from 3 sensor chips with random cell confluence. g, Normalized mass distribution of released single molecules obtained from the 3 chips. The inset shows the original distribution. h, Hitting rate as a function of confluency or cell density. The data is plotted in log-log scale and fitted linearly (solid line). Data within the same group were measured with one chip but using different regions of interest (ROIs). The 0 confluence was measured using a chip without cells. Error bars represent mean±s.d. The dashed line marks mean+2×s.d. of the 0 confluency. i, Control experiments using chips without cells or lysis buffer. From left to right: n=17 (on 3 chips), 37 (on 7 chips), and 28 (on 8 chips). The dashed line shows mean+2×s.d. of the cell-free group. *p<0.05; ****P<0.0001.

DEFINITIONS

Figure 1A:
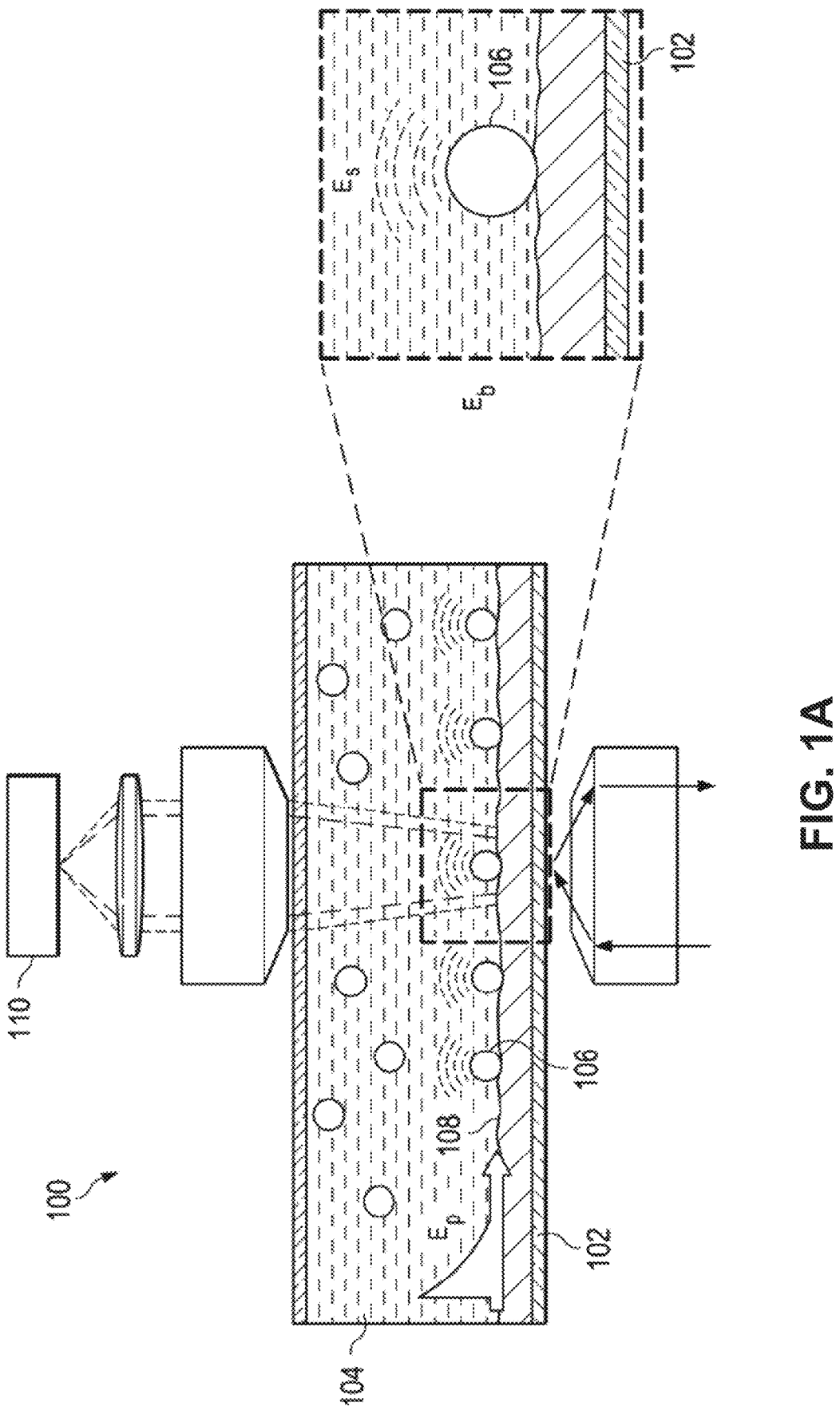
FIGS. 1A and 1B schematically show an exemplary objective-based plasmonic imaging system that can be used to detect single molecule binding to the surface of a sensor according to some aspects disclosed herein.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Antibody: As used herein, the term "antibody" refers to an immunoglobulin or an antigen-binding domain thereof. The term includes but is not limited to polyclonal, monoclonal, monospecific, polyspecific, non-specific, humanized, human, canonized, canine, felinized, feline, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda. The term "monoclonal antibody" refers to an antibody that displays a single binding specificity and affinity for a particular target, e.g., epitope.

Biomolecule: As used herein, "biomolecule" refers to an organic molecule produced by a living organism. Exemplary biomolecules, include without limitation macromolecules, such as nucleic acids, proteins, peptides, oligomers, carbohydrates, and lipids.

Fluidic Material: As used herein, "fluidic material" refers to a liquid substance that continuously flows or deforms under an external force or applied shear stress.

Ligand: As used herein, "ligand" refers to a substance that forms a complex with another molecule, such as a biomolecule.

Nucleic Acid: As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Protein: As used herein, "protein" or "polypeptide" refers to a polymer of at least two amino acids attached to one another by a peptide bond. Examples of proteins include enzymes, hormones, antibodies, and fragments thereof.

DETAILED DESCRIPTION

In some aspects, the present disclosure provides a label-free imaging approach to measure intracellular proteins and protein complexes. The principle resembles SiMPull, except that the proteins are imaged without labels, so the disclosed technique is sometimes referred to herein as Label-Free Single-Molecule Pulldown (LFSMP). In some embodiments of LFSMP, the molecules released from cells are imaged using plasmonic scattering microscopy (PSM), a single-molecule platform that measures the scattering light from each individual molecule. In some embodiments, the scattered light intensity is proportional to the molecular weight, with a dynamic range from ~100 kDa to several MDa, making LFSMP particularly suitable for protein complex detection. In some embodiments, the label-free feature also enables kinetics analysis of the captured complexes. Compared to western blot technologies, for example, LFSMP measurements can be performed using as few as several cells. And, LFSMP typically does not denature the native structure of protein complexes, thus the composition and function of the complexes are retained. These and other attributes of the present disclosure will be apparent upon a complete review of the specification, including the accompanying figures.

Systems and methods described herein include implementations of near field optical imaging in which the near field is created by surface plasmon resonance (SPR) or total internal reflection (TIF). Rather than detection of reflected light, however, scattered light from the sample molecules and sensor surface is detected. Light scattered by a molecule in free space scales with the $6^{th}$ power of the molecular diameter. For this reason, the scattered light intensity diminishes quickly with the molecular size, making it difficult to image single molecules. To overcome this issue, a sensor surface with a selected roughness is used, such that the sensor surface scatters light with a magnitude comparable with that of the scattered light from the target single molecules. There are different ways to define surface roughness, and one of which is given by $$\sqrt{\frac{1}{n}\sum_{i=1}^{n} y_i^2} \qquad (1)$$

where $y_i$ is the height at position i, and n is the number of positions. Using this definition, the surface roughness of a gold surface is −1.5 nm.

In some implementations, a roughness of the sensor surface is in a range of about 1 nm to about 100 nm. The interference of light scattered from the protein and sensor surface produces an image contrast that scales with the $3^{rd}$ power of the molecular diameter. This slows down the decay in image contrast with the molecular size, which favors imaging of small objects (e.g., single protein molecules).

Rough features and impurities on the sensor surface, and features associated with imperfect optics, all contribute to image contrast, which can mask weak images of single molecules. As described herein, a differential-integral imaging processing algorithm is used to subtract out background features that contribute to image contrast above from each frame of the time sequence images and integrate the differential images to recover the binding and unbinding of single protein molecules on the sensor surface. A drift or motion correction algorithm is introduced to track the drift or motion pattern of one or more features on the sensor surface and correct the drift or motion from each image frame, thereby reducing the impact of drift in position of the sensor surface or the optics or mechanical vibrations of the environment. Binding kinetics are assessed by counting the individual target molecules on the sensor surface. This digital counting approach allows a precise measurement of binding kinetics. In addition, this approach obviates the need to measure the shift in the surface plasmon resonance angle (determined not only the number of the molecule that bind to the sensor surface, but also by the size of the molecule) either directly or indirectly.

SPR-based single molecule analysis. Implementations include plasmonic imaging systems and methods for SPR-based single molecule analysis. In some cases, the plasmonic imaging system includes an objective. In some cases, the plasmonic imaging system includes an optical prism rather than an objective.

FIG. 1A is a schematic of objective-based plasmonic imaging system 100 that can be used to detect single molecule binding to the surface of a sensor. Surface plasmonic waves ($E_p$) are excited by light from the bottom of a gold-coated glass slide and scattering of the plasmonic waves by a particle or protein ($E_s$) and by the gold surface ($E_b$) is collected from the top to form a plasmonic scattering microscopy (PSM) image. In one example, a sensor includes a metal (e.g., gold) coated glass substrate 102. A solution 104 of the target molecule 106 (e.g., a protein) is introduced to the sensing surface (e.g., via a flow cell). The sensor surface can be functionalized with capture probes 108 for detection of target molecules or particles (e.g., specific proteins). The light scattered from the target molecules or particles is collected from the top camera 110. The conventional surface plasmon resonance image can be obtained from a bottom camera simultaneously.

In some implementations, the objective of the system in FIG. 1A is replaced with an optical prism. The prism has a top surface on which the sensor is placed. The prism also has a flat surface for the introduction of incident light and a second flat surface for light reflected from the sensor surface to exit the prism.

Figure 1B:
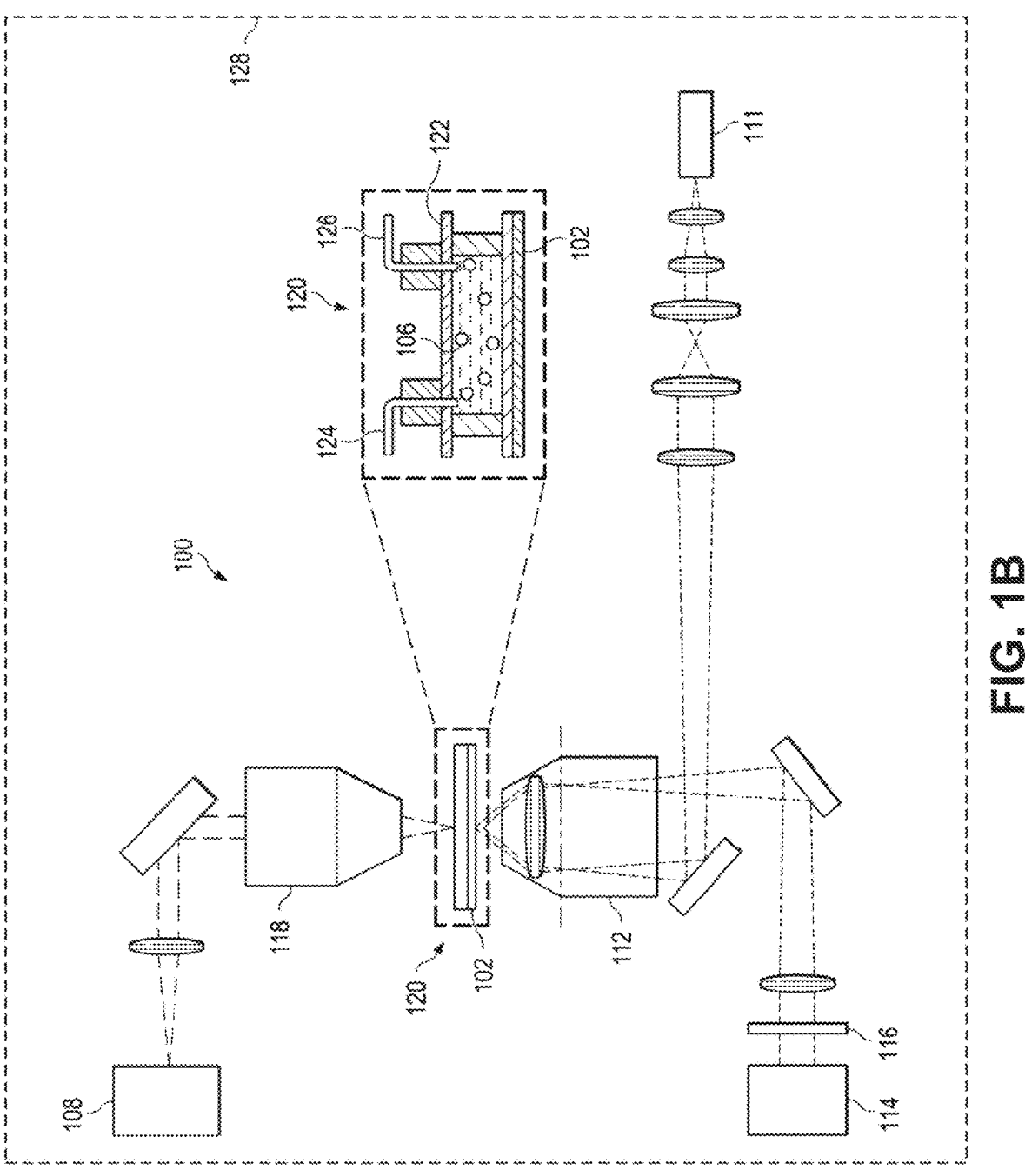

FIG. 1B is a more detailed view of objective-based plasmonic imaging system 100. Optical setup for simultaneous PSM and SPR imaging, where light from a superluminescent diode (SLD) 111 is conditioned and directed via a 60× objective (NA=1.49) 112 onto a gold-coated glass slide 102 mounted on the objective via refractive index matching oil. Light reflected from the gold-coated glass slide 102 is detected by camera 114 (Pike F-032B), which is equipped with an optical attenuator 116 (ND30A, Thorlabs, Newton, NJ) to avoid overexposure. The incident light angle is adjusted to surface plasmon resonance, at which the reflected light reaches a minimum. Simultaneously, light scattered from the gold surface is collected by a 50× objective (NA=0.42) 118 and detected by camera 108 (MQ003MG-CM, XIMEA) placed on top of the gold surface. The incident light intensity is 3 kW/cm² or less. Camera 114 measures the traditional SPR and camera 108 records PSM images. Flow cell 120 includes gold-coated glass slide 102, cover glass 122, inlet 124, and outlet 126. In one embodiment, a distance between gold-coated glass slide 102 and cover glass 122 is about 50 microns. However, this distance can be different in other embodiments.

System 100 can include controller 128. Controller 128 can be configured to control one or more components of system 100 (e.g., cameras 108, 114, SLD 111), to control fluid flow to and away from system 100, and to process data or images collected one or more components of system 100 (e.g., cameras 108, 114). In some cases, controller 128 can be used to correct for mechanical drift in system 100.

In one example, gold-coated glass slides were prepared by evaporating 2 nm thick chromium on BK-7 glass slides, followed by 47 nm gold. Before loading into the vacuum chamber for chromium and gold evaporation, the BK-7 glass slides were cleaned by acetone and by deionized water thoroughly. The gold surfaces were examined by Atomic Force Microscopy (AFM), showing islands of variable sizes.

TIF-based single molecule analysis. Systems for TIF-based molecule analysis can be similar to those for SPR-based single molecule analysis, with a sensor surface that is free of a metallic coating. When the incident angle is near or larger than a critical angle, it is totally reflected from the sensor surface, which has been referred to as total internal reflection (TIF). Under this condition, an evanescent field (also referred to as near field) appears on the sensor surface, which decays exponentially into the solution on top of the sensor surface. As in the SPR implementations, this evanescent field is scattered by single molecules on the sensor surface, and the interference light scattered by the single molecules and by the sensor surface produces image contrast.

Effect of heating due to incident light. To maximize the signal to noise ratio, high incident light intensity is preferred, which, however, causes heating of the sensor surface and leading to instability of the optical system and structure of the target molecules. This problem can be overcome as described herein by using the same fluidics for flowing in and out sample molecules to cool down the heating.

Single proteins are directly imaged with a SPR imaging system, and detected and identified based on their sizes and specific binding to the corresponding antibodies. Quantification of protein binding kinetics is demonstrated by digitally counting and analyzing the binding and unbinding of individual molecules.

The SPR imaging system has several unique features. First, the evanescent field intensity is localized within −100 nm from the SPR sensor surface (e.g., gold-coated glass slide), making it immune to interference of molecules and impurities in the bulk solution, thus particularly suitable for studying surface binding. Second, there is a large enhancement (20-30 times) in the field near the sensor surface, which is responsible for the high sensitivity of SPR. Finally, the resonance condition of SPR depends on the refractive index near the sensor surface, such that surface charging, small molecules or ions, and biochemical reactions that do not scatter light strongly can also be measured with the same setup from the simultaneously recorded traditional SPR images.

Referring to FIG. 1A, surface plasmonic waves are excited by directing light at an appropriate angle via an oil-immersion objective onto a gold-coated glass slide placed on the objective. In traditional SPR, light reflected from the gold surface is collected to form an SPR image, which is described by $$I \sim |E_F + E_P + E_r|^2, \qquad (2)$$

where $E_p$ is the plasmonic wave excited by the incident light, $E_s$ describes the scattering of the plasmonic wave by a protein on the sensor surface, and $E_r$ is the reflection of the incident wave from the backside of the gold surface. The SPR image contrast is determined by the interference between the planar plasmonic wave and the spherical scattered plasmonic wave, given by $2|E_p||E_s|\cos(\ominus)$, where Q is the phase difference between the two waves, which produces a spot at the location of the protein with a parabolic tail. $E_s$ is proportional to the optical polarizability of the protein, which scales with the mass of the protein or $d^3$, where d is the diameter.

$E_r$ in Eq. 2 produces a large background in the SPR image, which masks the weak scattered wave ($E_s$) from a single protein. To overcome this difficulty, plasmonic waves scattered by the protein were imaged with a second objective placed on top of the sample, in addition to recording the traditional SPR images from the bottom. This avoids the collection of the strong reflection and also eliminates the parabolic tail, providing a high contrast image of the protein. At first glance, the image contrast should scale according to $|E_s|^2 \sim d^6$. This would lead to a rapid drop in the image contrast with decreasing d, making it challenging to detect small proteins. However, the gold surface is not atomically flat. Atomic Force Microscopy (AFM) has revealed nm-scaled gold islands, which scatter the surface plasmonic waves and produce a background ($E_b$) also collected by the top objective. Consequently, the plasmonic image is given by $$I \sim |E_b + E_o|^2 = |E_b|^2 + 2|E_b||E_s|\cos(\beta) + |E_s|^2, \qquad (3)$$

where $\beta$ is the phase difference between light scattered by the protein and by the gold surface. The interference term, $2|E_b||E_s|\cos(\beta)$, in Eq. 3 produces image contrast that scales with $d^3$, or the mass of the protein. To differentiate this plasmonic imaging method from the traditional SPR imaging, it is referred to as PSM.

To obtain a high contrast PSM image, $|E_b|^2$ is removed from Eq. 3, which is achieved with the following imaging processing flow. Starting from the raw images captured with a high frame rate, the image frames are averaged (e.g., over 50 ms) to remove pixel and other random noise in the images. Differential images are then obtained by subtracting a previous frame from each frame, or I(N)−I(N−1), where I(N) and I(N−1) are the $N^{th}$ and $(N-1)^{th}$ image frames. The subtraction removes background features and captures the binding of a protein to the surface on $N^{th}$ image frame. To view all the proteins on the surface on $N^{th}$ frame, the differential images are integrated from 1 to N. Due to thermal and mechanical drift of the optical system, a drift correction mechanism is introduced to ensure effective removal of the background.

Referring to FIG. 2, data processing protocol 200 of PSM images includes capturing 202 raw images, averaging 204 the image sequence captured at a high frame rate to remove pixel and other random noise in the images, introducing 206 a drift correction mechanism to correct the thermal and mechanical drift of the optical system, obtaining 208 differential images by subtracting the previous frame from the present frame, applying 210 a low-pass spatial filter to further minimize noise to the differential image sequence, removing 212 image frames without binding or unbinding events from the filtered differential image sequence, and integrating 214 the image sequence from first frame to $N^{th}$ frame to produce an image sequence, I(N).

The evanescent field associated with SPR decays exponentially from the surface (z-direction) into the solution. In other words, the scattering of the evanescent field by a finite size object depends on the distance (z) from the surface, and is given by, $$E_{EP} = E_0 \int_0^D \pi(Dr - z^2)e^{-1} dz. \qquad (4)$$

where $E_O$ is a constant, z is distance from the gold surface, D is the diameter of the particle, and I is the decay length of the evanescent field, which is approximately 200 nm. Taking this z-distance dependence into account, the effective diameters of the 26, 44, 65, 99, 145, and 194 nm polystyrene nanoparticles used in this work should be 25.4, 42.4, 61.6, 91.3, 129.1, and 166.3 nm, respectively. The need of this correction decreases with the size and the correction becomes insignificant for proteins.

In addition to the exemplary systems disclosed herein, the present disclosure also provides various methods that can be implemented using those systems. In some embodiments, for example, the present disclosure provides methods of detecting unlabeled biomolecules. In some embodiments, these methods include disrupting a cell population sufficient to release at least some unlabeled biomolecules from at least one cell in the cell population to produce released biomolecules in which the cell population is disposed on a first inner surface of a chamber that is disposed substantially within a fluidic device and in which the chamber comprises a fluidic material. These methods also includes binding at least a portion of the released biomolecules to a second inner surface of the chamber to produce one or more surface-bound biomolecules, introducing an incident light toward the second inner surface of the chamber concurrent with, and/or after, producing the surface-bound biomolecules, and detecting light scattered by the surface-bound biomolecules over a first duration to produce a set of biomolecule imaging data.

In other aspects, the present disclosure provides fluidic devices that are of use in performing the methods disclosed herein. In some embodiments, the fluidic devices include a body structure that defines at least one chamber disposed substantially within the body structure in which the chamber comprises a fluidic material and at least first and second inner surfaces, in which a cell population is disposed on the first inner surface, and in which the second inner surface is coated with a metallic layer that is configured to create surface plasmon resonance when incident light is introduced toward the second inner surface at a suitable incident angle via a second outer surface of the chamber. In some embodiments, the fluidic devices further include at least one inlet port and at least one outlet port that both fluidly communicate with the chamber. In some embodiments, the metallic layer comprises gold (Au). In some embodiments, the second surface comprises a plurality of biomolecule capture moieties that are capable of binding unlabeled biomolecules when the unlabeled biomolecules are released from at least one cell in the cell population. In some embodiments, the biomolecule capture moieties are selected from, for example, antibodies, aptamers, receptors, and/or the like.

In other aspects, the present disclosure also provides computer readable media that include non-transitory computer executable instruction which, when executed by at least electronic processor, perform at least: disrupting a cell population sufficient to release at least some unlabeled biomolecules from at least one cell in the cell population to produce released biomolecules, wherein the cell population is disposed on a first inner surface of a chamber that is disposed substantially within a fluidic device and wherein the chamber comprises a fluidic material, such that at least a portion of the released biomolecules bind to a second inner surface of the chamber to produce one or more surface-bound biomolecules; introducing an incident light from a light source toward the second inner surface of the chamber; and detecting light scattered by the surface-bound biomolecules over a duration to produce a set of biomolecule imaging data to thereby detect the unlabeled biomolecules using a detector.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 208 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Figures 3A, 3B:
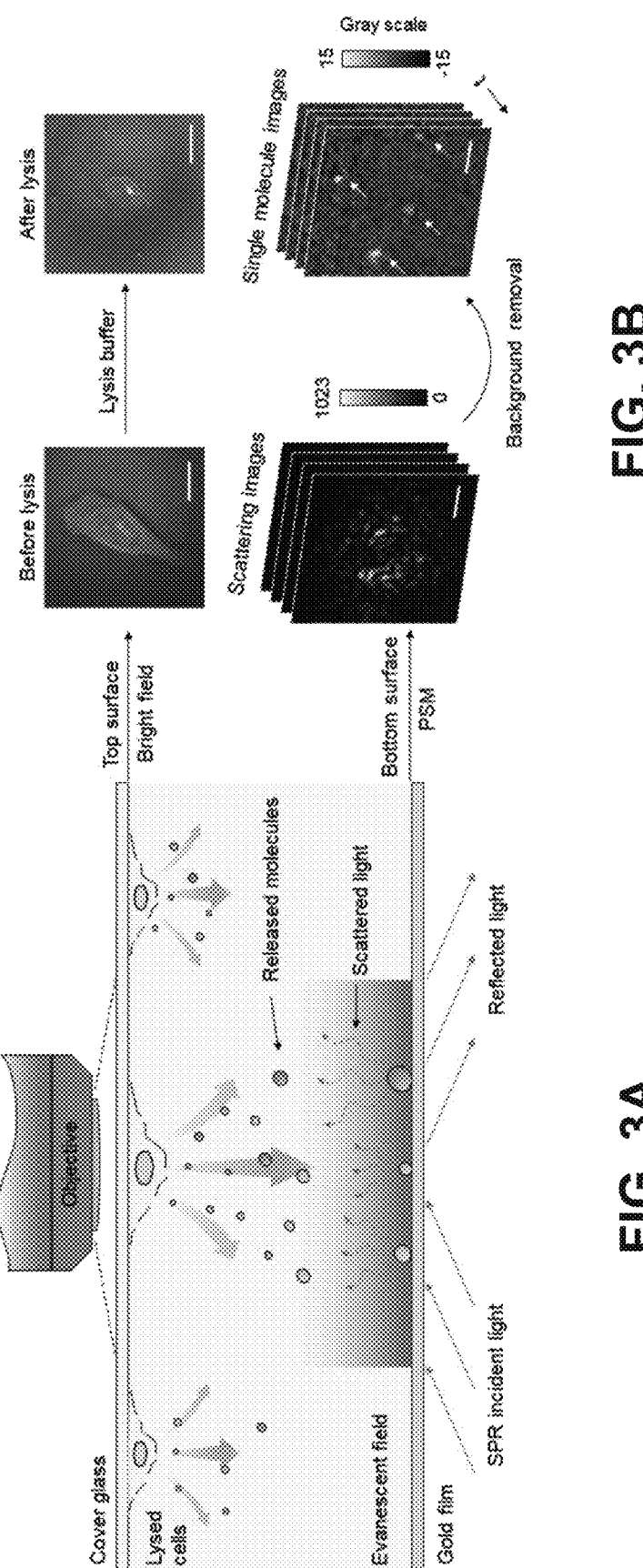

Example: Label-Free Single-Molecule Pulldown for the Detection of Released Cellular Protein Complexes Results Imaging Single Molecules from Lysed Cells The stability of intracellular proteins and complexes is known to decrease when extracted to extracellular environments. To collect the released molecules rapidly and efficiently after cell lysis, we fabricated a thin flow channel (51 μm in height) with adherent live cells cultured on the top glass surface (FIG. 3A). After introducing lysis buffer, the cells are lysed in situ, and the intracellular molecules, including proteins and protein complexes, are released into the channel and diffuse to the bottom gold film surface. We use PSM to image the released single molecules at the bottom. Briefly, an incident laser is coupled to the gold surface via a prism, which excites surface plasmon resonance (SPR) and the associated evanescent field on the surface. The scattered light by the molecules as well as by the surface roughness within the field are collected by an objective on top of the flow channel, and imaged by a CMOS camera (FIG. 3B, bottom panels). Single molecule images are obtained after background removal (see below). The top surface of the channel can be imaged using the same objective under bright field to locate the cell and observe the morphology change before and after lysis (FIG. 3B, top panels). The evanescent field at the bottom is confined to the surface within ~100 nm, thus the cells and molecules in the bulk solution could not be imaged by PSM.

Figure 3C:
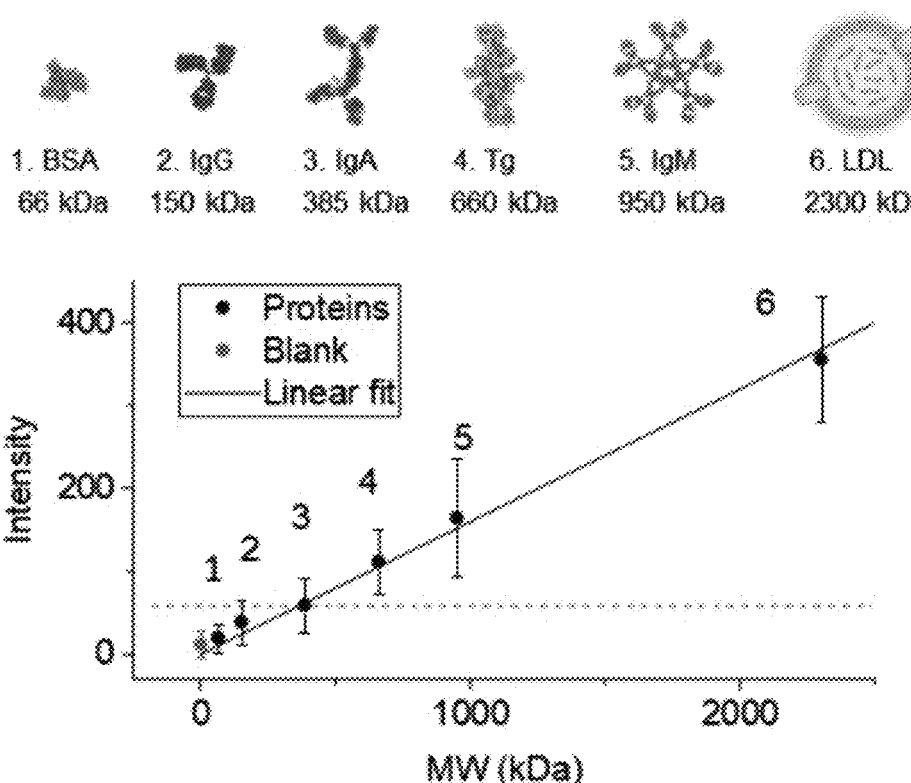

To evaluate the capability of the PSM system for single molecule imaging, we first measured several pure protein samples with molecular weight (MW) ranging from 66 kDa to 2.3 MDa. FIG. 3C shows a linear relationship between the MW and image intensity of the proteins, which is expected according to the PSM imaging principle. Among the 6 measured proteins, immunoglobulin G (IgG), immunoglobulin A (IgA), thyroglobulin (Tg), immunoglobulin M (IgM), and low-density lipoprotein (LDL) could be readily imaged with single-molecule resolution. However, bovine serum albumin (BSA) did not have enough signal-to-noise ratio (SNR) due to its small size and insufficient scattered photons. A blank sample containing only phosphate buffered saline (PBS, the solvent of the protein samples) was used to determine the system noise level. The mean+3× standard deviation (s.d.) of the blank was defined as the detection limit, which was 385 kDa in MW. We use this number as a threshold to exclude small proteins or low SNR spots for the following protein complex measurements.

Figure 3D:
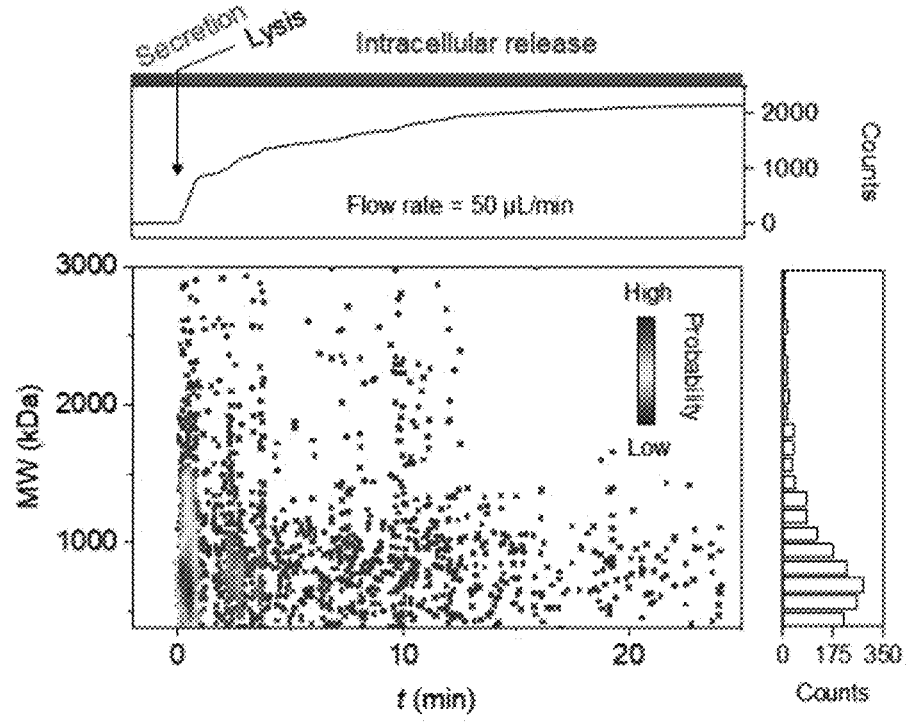

We next studied the cell lysis process with PSM. The cells were cultured on the top surface at a confluence of 10%, or 1.25 cells/$10^4$ $\mu m^2$, and the bottom surface was blocked with BSA. Live cell imaging buffer was flowed in the channel at a constant flow rate of 50 $\mu L/min$ to maintain cell viability. Before cell lysis, only a few secreted molecules were imaged on the bottom surface with a hitting rate of <1 hit/min, which was due to the low level of macromolecule secretion. In contrast, upon introducing cell lysis buffer, a sudden increase of released molecules was observed with ~1000 hits/min, indicating immediate lysis of the cells. Some extremely strong scattering signals could be occasionally observed due to cell debris and organelles. The hit rate is proportional to the protein concentration, as confirmed by a calibration measurement, and 1000 hits/min is equivalent to 550 nM according to the calibration. FIG. 3D (top panel) shows the total number of single-molecule hits before and after the lysis. The release was most active in the first 1 min, and then gradually declined over the next 25 min due to the depletion of intracellular molecules. The MW of each single molecule is determined using the curve in FIG. 3C, and a release mass profile is shown in FIG. 3D (bottom panels). Note that the mass profile only shows molecules with MW>385 kDa, because smaller molecules with insufficient SNR are discarded. Another observation is that larger molecules (e.g., >1500 kDa) are more likely to release in the first 10 min. After 15 min, over 95% of the molecules are smaller than 1000 kDa. This might be caused by the disassembly of protein complexes after the breakdown of intracellular environment.

Figure 3E:
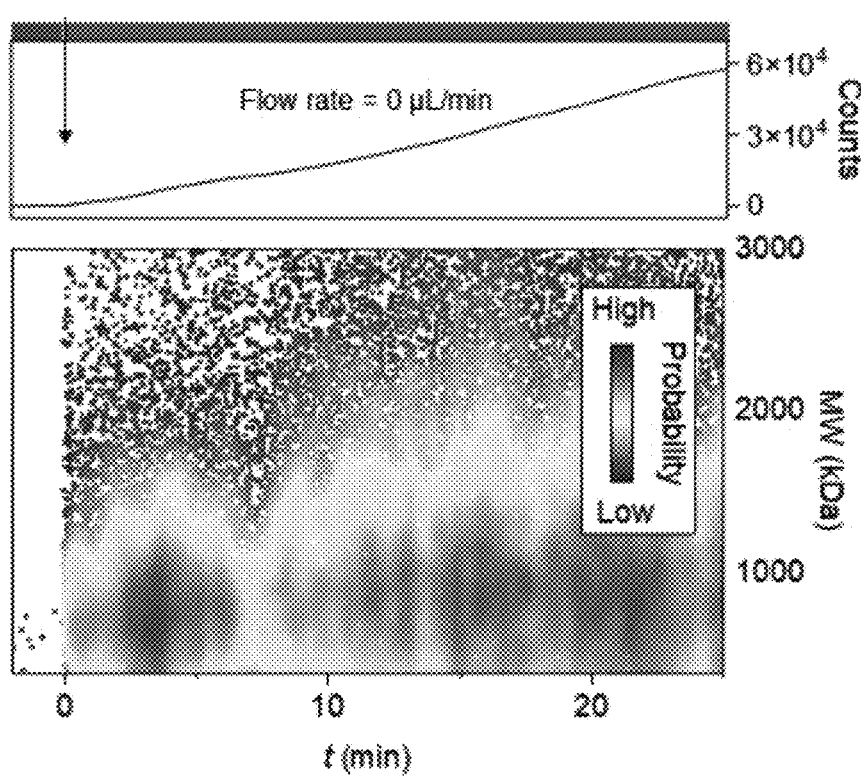
Figure 3F:
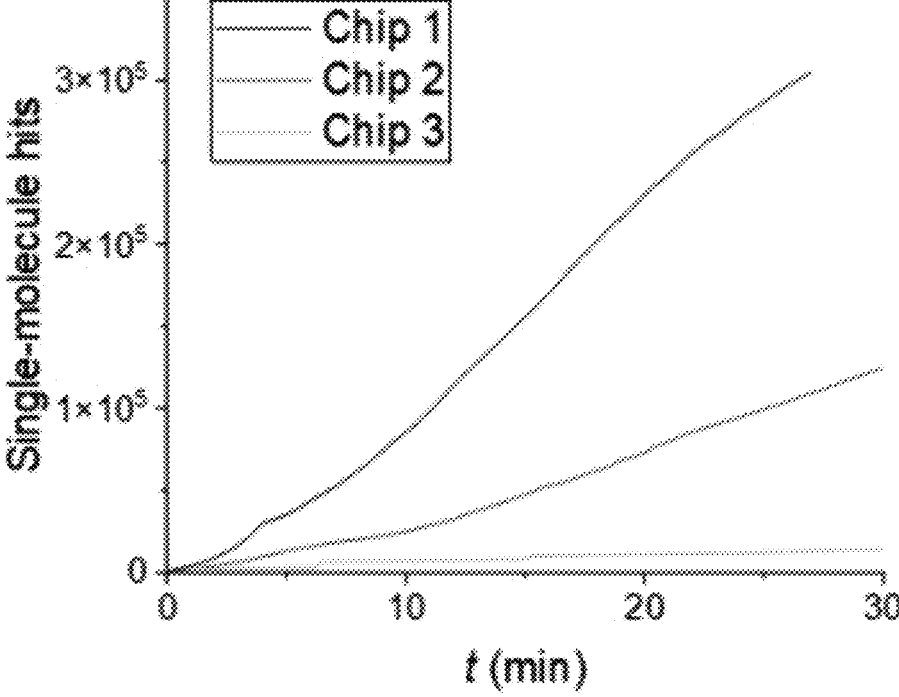

Because most molecules are flushed away quickly by the flow after the lysis, their in-channel retention time is limited, which reduces the pulldown probability. This is particularly undesirable when measuring low-abundant proteins and complexes. To solve this problem, we stopped the flow once the channel was filled with lysis buffer, such that most of the released molecules were trapped inside the channel and could have more interactions with the surface. FIG. 3E shows the cell lysis process with the channel closed (cells at 15% confluence). Although the lysis was finished in 1 min, the released molecules kept hitting and interacting with the surface with no decline even after 25 min. Therefore, we adopted this method for our measurements to increase the reaction efficiency. Another important factor that affects the hitting rate is cell confluence. By measuring 3 sensor chips with different confluence, we found substantial variations in the hitting rate (FIG. 3F). However, the mass distribution of the 3 measurements shows similar profiles, suggesting that the MW of released molecules is irrelevant to the confluency (FIG. 3G). To establish quantitative relationship between cell confluence and single molecule hitting rate, we counted the number of molecules at different cell confluences from 1% to 60% (FIG. 3H). A control experiment was conducted using a channel without cells with 3.7±1.8 hits/min detected, which was solely due to the impurities in the buffer. The detection limit, defined by mean+2×s.d., is equivalent to 0.40% confluence or ~5 cells in a 1 $mm^2$ region. We have repeated the lysis measurement for >25 times and summarized the result in FIG. 3I. The plot shows the comparison of hitting rate between lysed cells and controls (unlysed or without cells), where the lysed cells have markedly more molecules released. The unlysed cells were also found to secret molecules, but at a much lower level.

Specific Detection of Single Protein Complexes

We studied the mammalian target of rapamycin (mTOR) to demonstrate specific pulldown of single molecules from lysed cells. mTOR is an intracellular protein that plays a central role in regulating metabolism, growth, and proliferation, by forming two structurally and functionally distinct complexes, mTOR complex 1 (mTORC1) and mTOR complex 2 (mTORC2). Malfunction of mTORC has been linked to diseases such as cancer and diabetes. Both mTORC1 and mTORC2 are multimeric complexes with molecular weights estimated to be ~1000 kDa and 1500-2000 kDa, respectively.

Figures 4A, 4B, 4C:
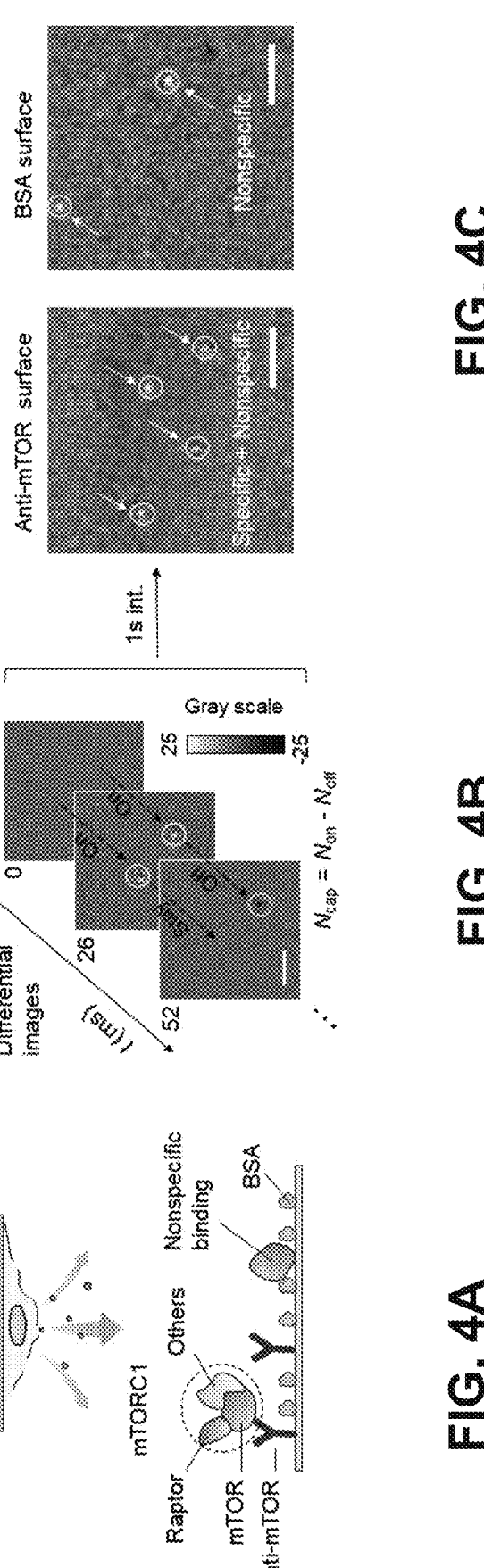
FIGS. 4A-4G. Specific detection of released single mTORC1. a, mTORC1, an intracellular protein complex consisting of mTOR, Raptor, and other components is specifically captured to the anti-mTOR functionalized surface. Although the surface is blocked with BSA, some large molecules can still bind to the surface nonspecifically and imaged by PSM. b, Representative differential images showing the dynamic binding and unbinding of single protein complexes. Scale bar, 3 μm. The bright spot and the dark spot in the image indicate the molecule hits or leaves the surface, respectively. The total number of captured molecules ($N_{cap}$) in a measurement is defined by $N_{cap}=N_{on}-N_{off}$. c, Integration of the differential images for 1 second. The arrows mark the position of the captured molecules. The left and right panels show the result of using anti-mTOR surface and BSA surface, respectively. Scale bar, 3 μm. d, The number of captured molecules on anti-mTOR surface and BSA surface. Each data point is obtained from an individual measurement; n=28 (on 9 chips) and 31 (on 10 chips) for the anti-mTOR and BSA groups, respectively. For each measurement, the cell confluence is random, and the detection time ranges from 30 s to 2 min. e, The positive correlation between $N_{cap}$ and $N_{on}$. f, Capture ratio ($R_{cap}=N_{cap}/N_{on}$) is used to describe the binding ability, with anti-mTOR showing a significantly higher ratio than BSA. **P<0.01. The data is fitted with normal distribution (solid curves). g, Representative mass distribution curves of released molecules (top) and captured molecules (bottom) for anti-mTOR and BSA surfaces.
Figure 4D:
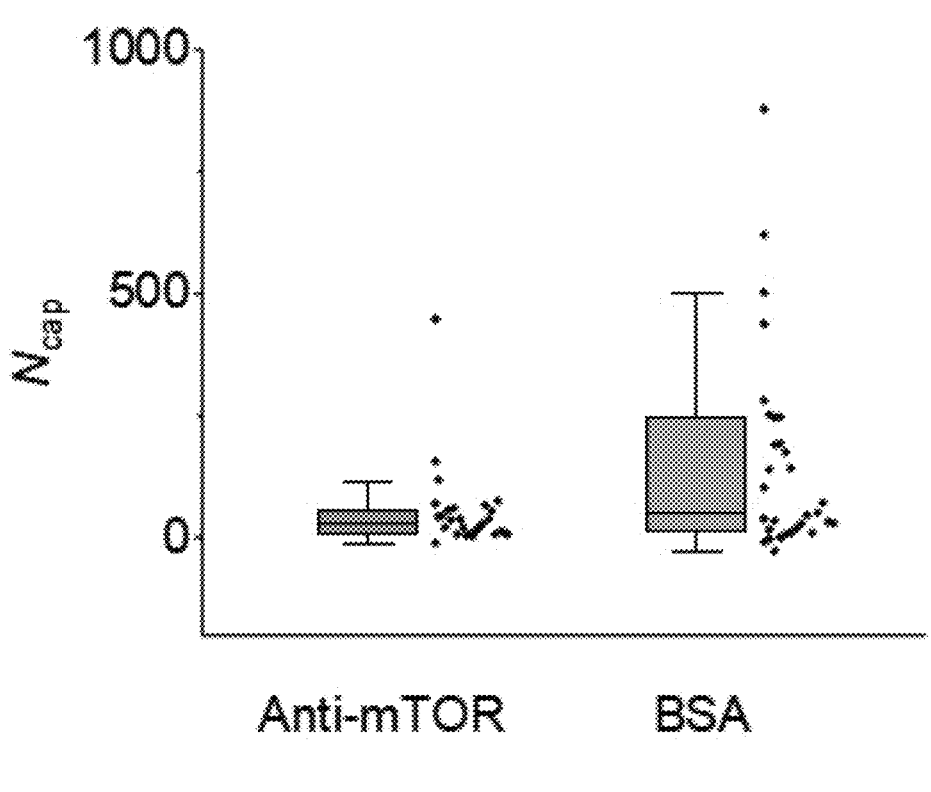
Figure 4E:
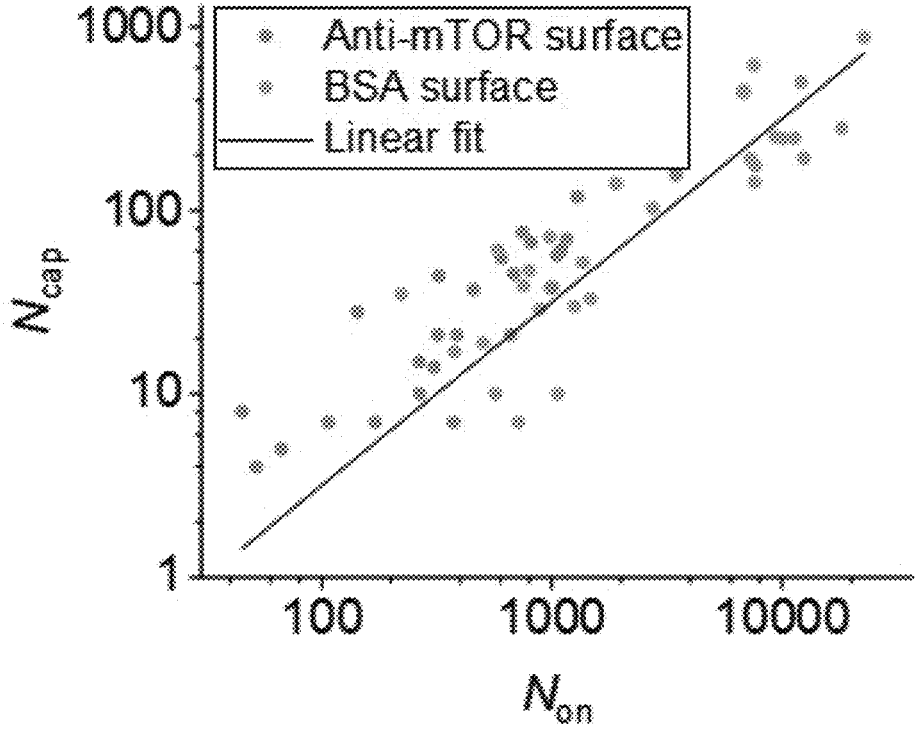
Figure 4F:
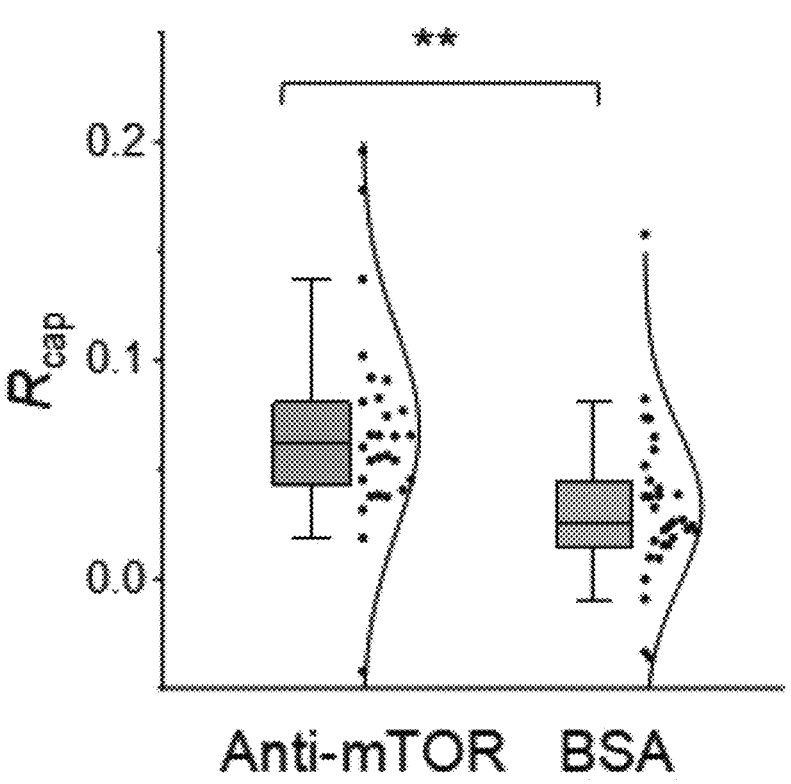
Figure 4G:
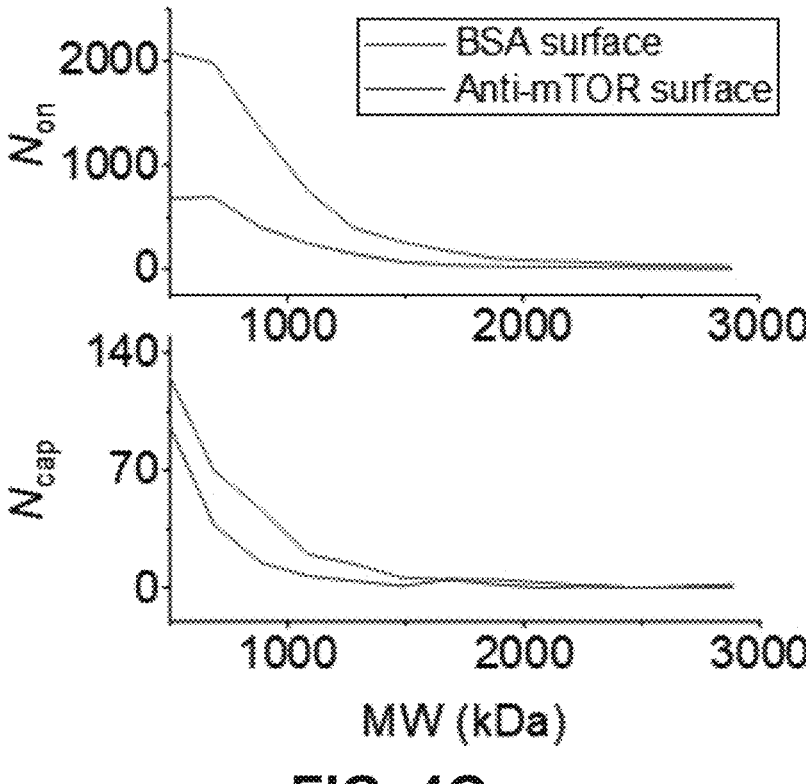

To capture mTORC, we functionalized the channel bottom surface with anti-mTOR and blocked the nonspecific sites with BSA, which is a common blocker in immunoassays (FIG. 4A). We determined the captured molecules by analyzing the binding and unbinding events. To be specific, an image sequence was recorded after cell lysis, and a differential image sequence was obtained by subtracting the previous frame from each frame. Common backgrounds were removed in the differential images so that the single molecules were revealed. An example is shown in FIG. 4B. Each bright spot indicates a single molecule hitting on the surface, while each dark spot is caused by the leaving of the molecule. By counting the total number of hitting ($N_{on}$) or leaving ($N_{off}$) events over a period of time, the net counts of captured molecules is obtained by $N_{cap}=N_{on}-N_{off}$. To check whether the captured molecules were caused by specific binding, we compared the $N_{cap}$ of the anti-mTOR coated surface and that of a BSA coated surface. Molecules bound to BSA should be nonspecific, thus the BSA surface serves as a negative control. As an illustration, FIG. 4C shows integration of the differential images over 1 s for the anti-mTOR surface and the BSA surface. Both surfaces have captured molecules, suggesting strong nonspecific binding of released proteins/complexes to BSA. We obtained $N_{cap}$ from >25 measurements and found anti-mTOR did not show a higher $N_{cap}$ statistically (FIG. 4D). Whereas this result does not mean we could not distinguish the specific binding and nonspecific binding. As discussed above, the total number of released molecules (or hits) are different for each measurement, which stems from variations in cell confluence, detection time, and lysis efficiency. In fact, $N_{cap}$ is positively correlated with the total hits ($N_{on}$) (FIG. 4E). As such, the real binding level should be $N_{cap}$ normalized by $N_{on}$. FIG. 2f shows normalized $N_{on}$ for anti-mTOR and BSA surfaces, where $R_{cap}=N_{cap}/N_{on}$. The data follows Gaussian distribution after normalization, and anti-mTOR is significantly higher than BSA with P=0.0015. The specific and nonspecific binding of mTORC can only be distinguished statistically because the cell lysate contains a wide spectrum of proteins and complexes, which are impossible to be blocked completely. We also studied the mass distribution of the released molecules (FIG. 4G). The MW profiles determined using all the released molecules are similar for anti-mTOR surface and BSA surface, which indicates surface modification does not affect MW detection. However, by plotting the MW distribution of the captured molecules, we did not find clear bands for mTORC at the predicted MW, because of the dominant nonspecific binding. It is also possible that some components in mTORC are partially dissociated in the lysis buffer. The specific capture of mTORC was also confirmed with a fluorescence measurement. Taken together, the above results suggest our method can pull down cellular molecules with good specificity.

Counting Single Protein Complexes for Signaling Pathway Study

Figure 5A:
FIGS. 5A-5G. Study AMPK/mTORC1 signaling pathway by counting single protein complexes. a, Schematic showing the protein complex in cell lysate is denatured into peptides using common SDS-PAGE preparation protocol. b, The mass profile of protein complexes detected in native cell lysate and denatured cell lysate. Both lysates were diluted 100 times with PBS and measured for 30 s. 4 measurements were performed using different sensor chips. The inset shows the total number of detected molecules. The error bar represents mean±s.d. c, A brief schematic of AMPK regulated mTORC1 signaling pathway. d, Normal cells and starved cells were lysed on top of anti-Raptor coated surface. $R_{cap}$ was determined from n=29 (on 3 chips) and n=18 (on 3 chips) measurements for normal cells and starved cells, respectively. e, Western blot result showing the Raptor level in normal cells and starved cells. f, Normal cells, starved cells, and AICAR treated cells were lysed on top of anti-phospho-Raptor functionalized surface, with n=24 (on 8 chips), 29 (on 4 chips), and 26 (on 5 chips) measurements, respectively. The $R_{cap}$ values were compared. g, Western blot result showing the phosphor-Raptor level in normal, starved, and AICAR treated cells. *P<0.05; P<0.01; *P<0.001; ****P<0.0001.
Figure 5B:
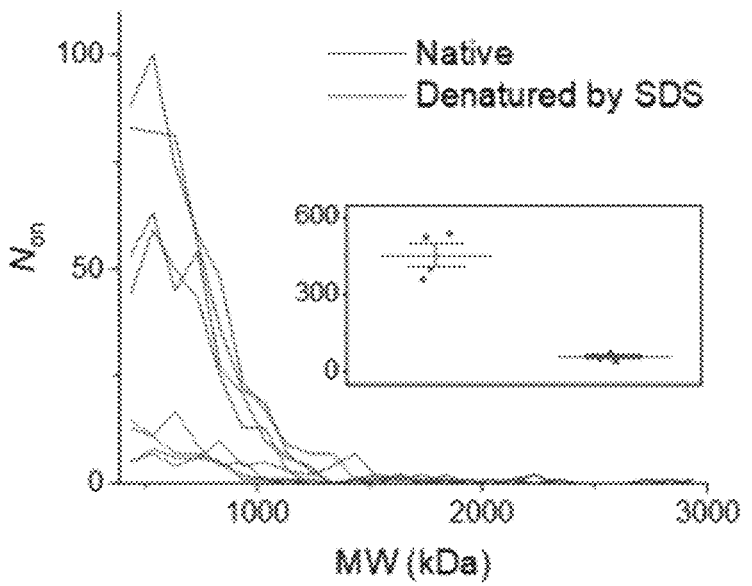

Protein complexes are involved in many signaling pathways. Probing such protein complexes usually requires denaturation, separation, and detection by SDS-PAGE and western blot, which totally breaks the native structure of the complexes (FIG. 5A). LFSMP provides a direct avenue to measure the protein complexes with minimal perturbation to the native structures, and with single-molecule sensitivity at the same time. To study the effect of denaturation on the size of protein complexes, we harvested cells from a culture flask (~1 million cells), lysed the cells and collected the lysate, and denatured a fraction of the lysate by incubating with SDS at 95° C. for 5 min. After dilution 100× with PBS, the sample was immediately loaded into the channel and imaged with PSM. Native lysate (also 100× diluted with PBS) without SDS treatment was measured as well. The counts and mass distribution are shown in FIG. 5B. 10 times more counts were found in the native lysates, which suggests over 90% protein complexes were denatured into smaller pieces after SDS treatment.

Figure 5C:
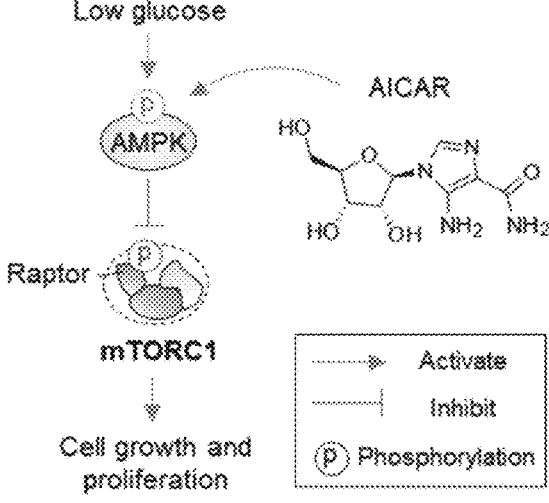
Figure 5D:
Figure 5E:
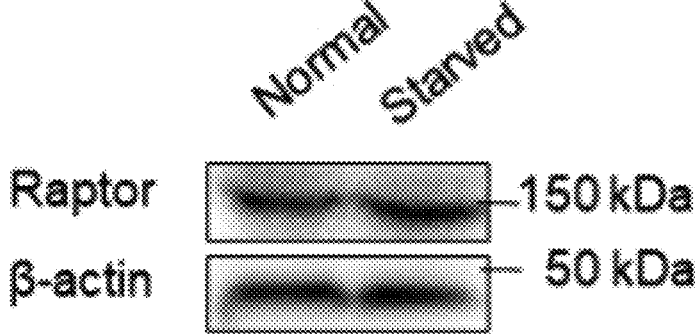

Next, we studied protein phosphorylation in the AMPK/mTORC1 pathway by pulling down the mTOR complexes. The AMPK/mTORC1 pathway is responsible for sensing energy and nutrients and regulating cell growth and proliferation (FIG. 5C). Under low glucose conditions, AMPK is activated via phosphorylation, which reduces the activity of mTORC1 by phosphorylating one of its component, Raptor. We used anti-Raptor coated chip to capture the released mTORC1 from normal cells and glucose-starved cells. Anti-Raptor can bind to both phosphorylated and unphosphorylated Raptor, thus reflects the total Raptor level. Markedly higher level of Raptor (P=0.0042) was found for the starved group (FIG. 5D). We also performed the same measurement using cell lysate with conventional SDS-PAGE and western blot, but little difference was found between the normal cells and starved cells (FIG. 5E). The western blot result agrees with previous findings that the total abundance of Raptor should not be altered by glucose deprivation.

Figure 5F:
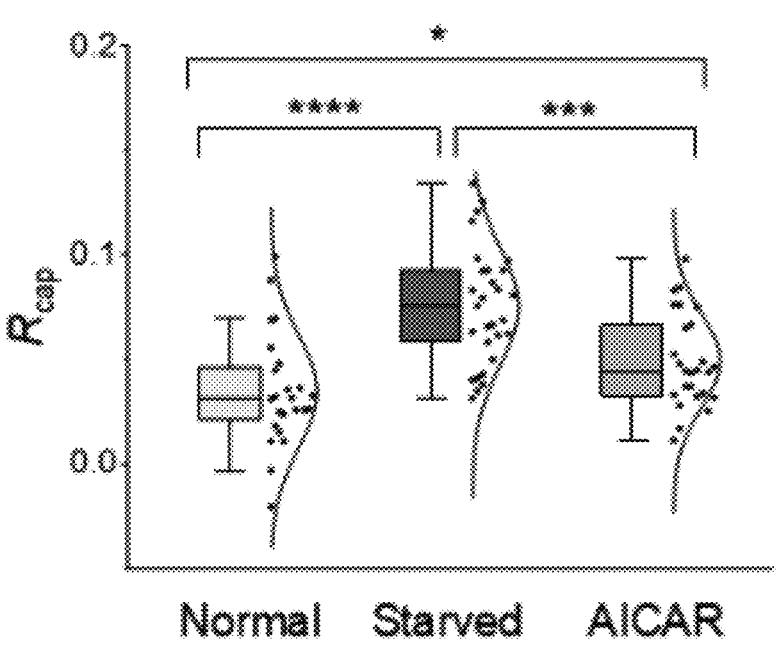
Figure 5G:
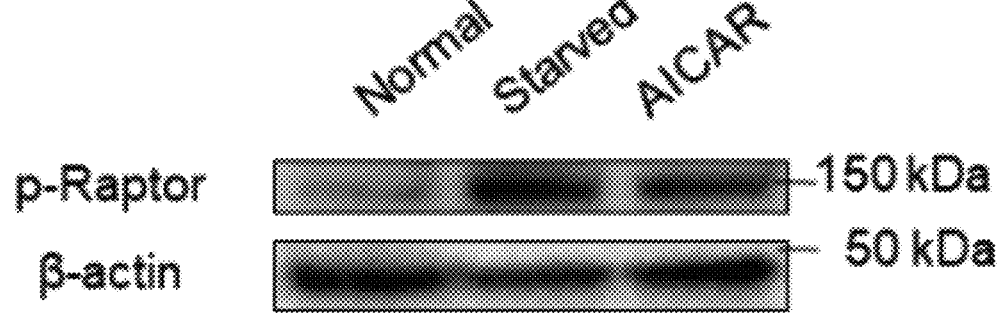

The deprivation of glucose also phosphorylates Raptor on Ser-792 in mTORC1. To investigate this process, we used phospho-Raptor antibody (anti-p-Raptor) for the pulldown measurement. A higher level of phosphorylated Raptor (p-Raptor) was observed in starved cells compared with normal cells (P=2.2×10$^{-6}$) (FIG. 5F), consistent with literature. We also performed a positive control by using 5-aminoimidazole-4-carboxamide (AICAR) to stimulate AMPK phosphorylation. As expected, the p-Raptor level was elevated compared with the normal cells (P=0.041), but still much lower than the starved group (P=4.2×10$^{-4}$). The results were confirmed by western blot using cell lysates (FIG. 5G). Together, our findings suggest that LFSMP can measure the native format of protein complexes and be combined with traditional western blot assays to decipher the role of protein complex in signaling pathways.

Figure 6A:
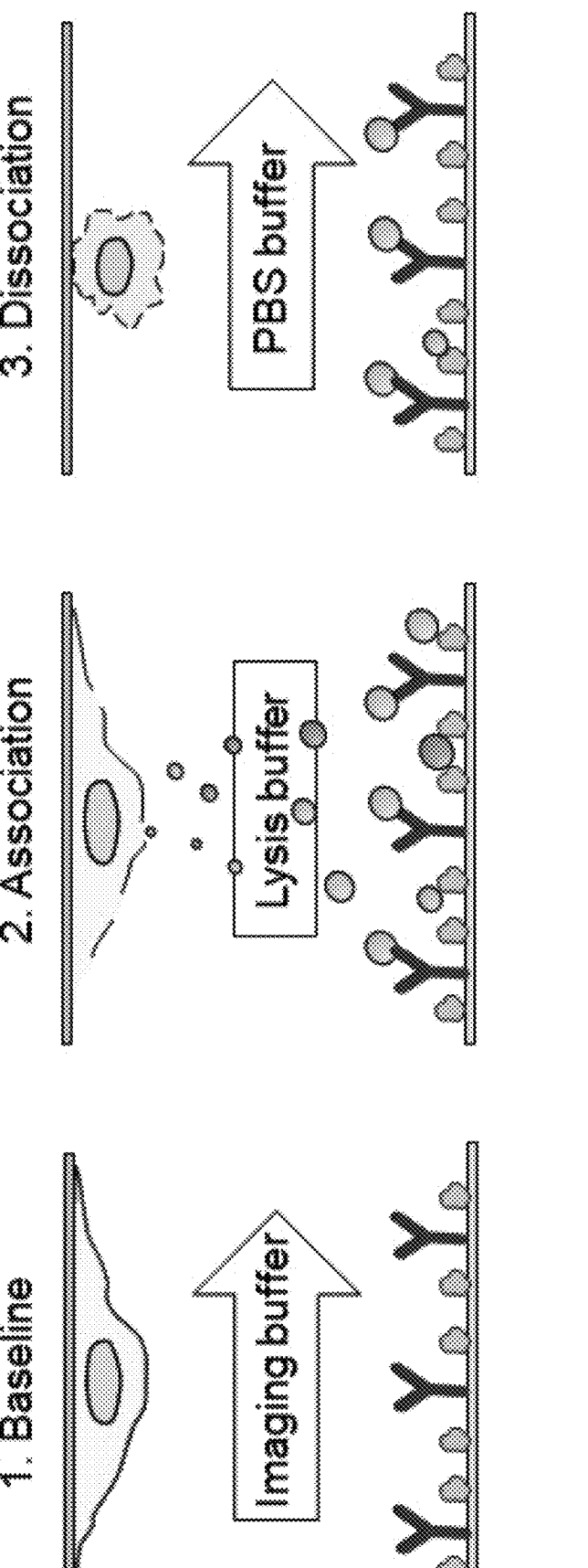
FIGS. 6A-6M. Real-time detection of mTORC1 binding to anti-mTOR. a, Detection protocol. The number of released complexes is continuously counted before (baseline), during (association), and after (dissociation) cell lysis. The arrow and the box indicate flow at 50 µL/min and no flow, respectively. b, The number of complexes binding to ($N_{on}$) or unbinding from ($N_{off}$) the anti-mTOR functionalized surface during the 3 processes. The complex concentration is calculated to be 424 nM. c, The number of complexes captured on the anti-mTOR surface ($N_{cap}$). The data is fitted to the first-order kinetics. The inset is a zoom-in of the section marked by the vertical line, showing single-molecule events. d, Correlating the binding ($t_{on}$) and unbinding timestamps ($t_{off}$) for individual complexes. The $t_{on}$ and $t_{off}$ from the same molecule is connected with a line, and the capture time is defined by the length of the line ($t_{cap}=t_{on}-t_{off}$). e, A zoom-in of d showing the binding and unbinding of representative single protein complexes with $t_{cap}>3$ min. f, Histogram showing the distribution of $t_{cap}$ determined in d. The molecule number for each bin is normalized by $N_{on}$. The histogram is fitted to an exponential decay model and the decay constant is 1.1 min. The reversible domain includes complexes that have both $t_{on}$ and $t_{off}$ identified during the measurement, while the irreversible domine illustrates complexes that only have $t_{on}$ and does not unbind within the 45 min dissociation phase. The dashed line is a time threshold at 3 min separating the reversible domain into weak binding regime and strong binding regime. g, Control experiment using BSA coated surface. h, A zoom-in of g showing representative single protein complexes with $t_{cap}>3$ min. i, Histogram showing the distribution of $t_{cap}$ determined in g. The decay constant is fitted to be 0.52 min. j, The ratio of strong binding in reversible interactions for anti-mTOR and BSA surfaces at different thresholds. k, Relative abundance between complexes captured by anti-mTOR and BSA using different thresholds. l, Mass distribution of captured complexes by anti-mTOR and BSA with different applied thresholds. m, The ratio of high MW (>2000 kDa) complexes using different thresholds.
Figure 6B:
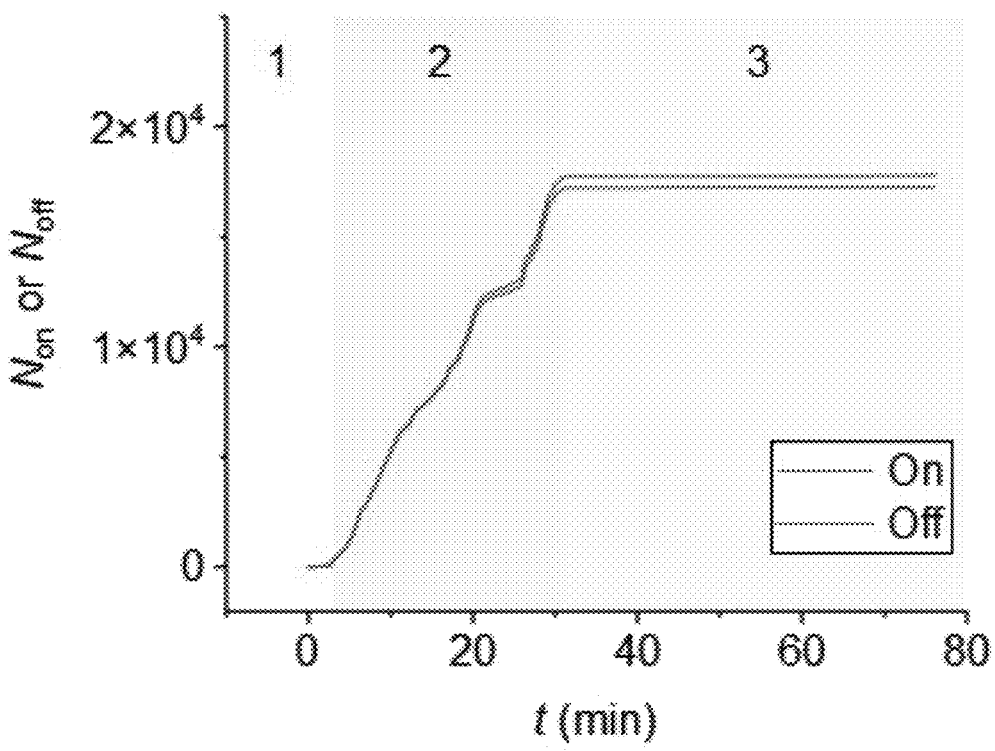
Figure 6C:
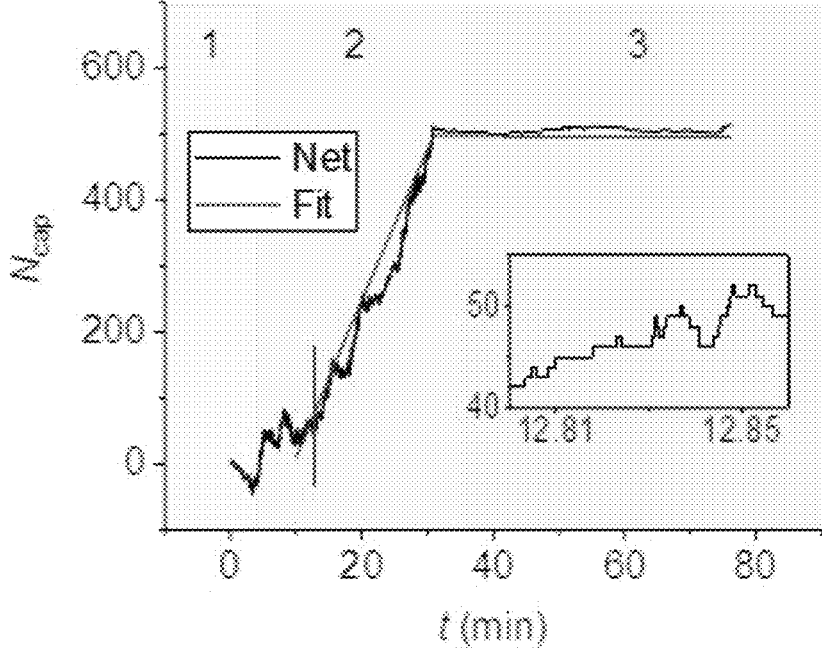

Differentiate Specific and Nonspecific Binding by Analyzing the Binding Kinetics The label-free feature of LFSMP allows us to analyze the single molecule binding in detail. Like the traditional ensemble SPR technique, we measured the binding between anti-mTOR and released mTORC in three phases, i.e., baseline, association, and dissociation (FIG. 6A). In the baseline phase, imaging buffer was flowed in the channel to keep cell viability. Only a few secreted proteins were found on the bottom surface. Then we initiated association phase by introducing lysis buffer into the channel. The flow was immediately paused after filling the channel with lysis buffer, and the released molecules were trapped in the channel. Finally, after sufficient single-molecule binding/unbinding events were recorded, PBS buffer was flushed over the surface to wash off the weakly bound molecules. Using the aforementioned counting method, we obtained $N_{on}$ and $N_{off}$ for the mTORC-anti-mTOR interaction as a function of time (FIG. 6B). Their difference, determined by $N_{cap}=N_{on}-N_{off}$, shows the net captured molecules or the binding kinetics curve (FIG. 6C). By fitting the curve to the first order kinetics, the association rate constant ($k_a$), dissociation rate constant ($k_d$), and dissociation constant ($K_D$) are found to be 1.9×10$^2$ M$^{-1}$s$^{-1}$, 1.0×10$^{-6}$s$^{-1}$, and 5.2 nM, respectively, which is strong binding. Note that the beginning of association is mass transfer limited due to cell lysis, but we neglect this effect considering the lysis was rapid (~1 min) compared with the whole association phase (~30 min).

The curve in FIG. 6C includes both specific and nonspecific binding, which is challenging for traditional ensemble biosensors to discriminate. We achieved this goal by correlating the spatiotemporal coordinates of the binding and unbinding events. For each binding or unbinding event, we extracted the spatial coordinates (x, y), image intensity (or MW), and the timestamp (t). After comparing the (x, y, MW, t) pairwise, we identified the binding event and unbinding event from the same single molecule. The criteria for assigning two events (1 and 2) to the same molecule are: 1) the distance between ($x_1$, $y_1$) and ($x_2$, $y_2$) is smaller than the diffraction limit; 2) the difference of MW should fall within the measurement error; and 3) binding always occurs before unbinding ($t_1 < t_2$). These analyses are feasible only if the imaging system is stable enough, otherwise the imaging region would drift away, and the molecule is lost. Our prism based PSM system owns excellent stability with negligible or correctable drift even after 1 hour of continuous image recording, which allows us to precisely locate the same molecule.

Figure 6D:
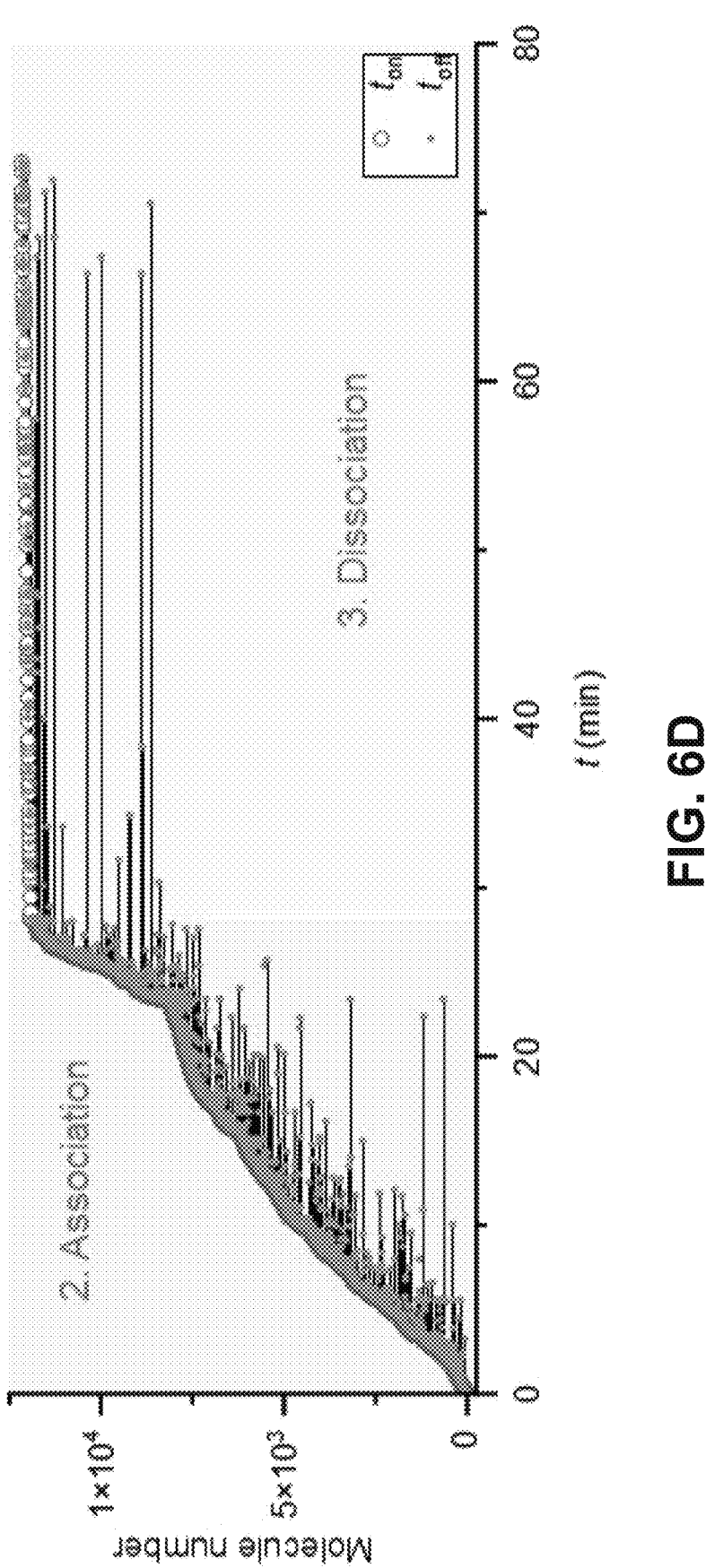
Figure 6E:
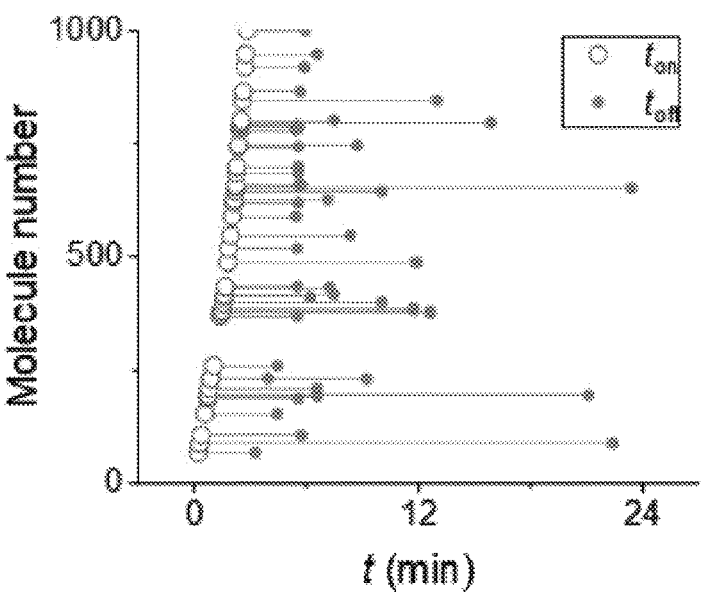
Figure 6F:
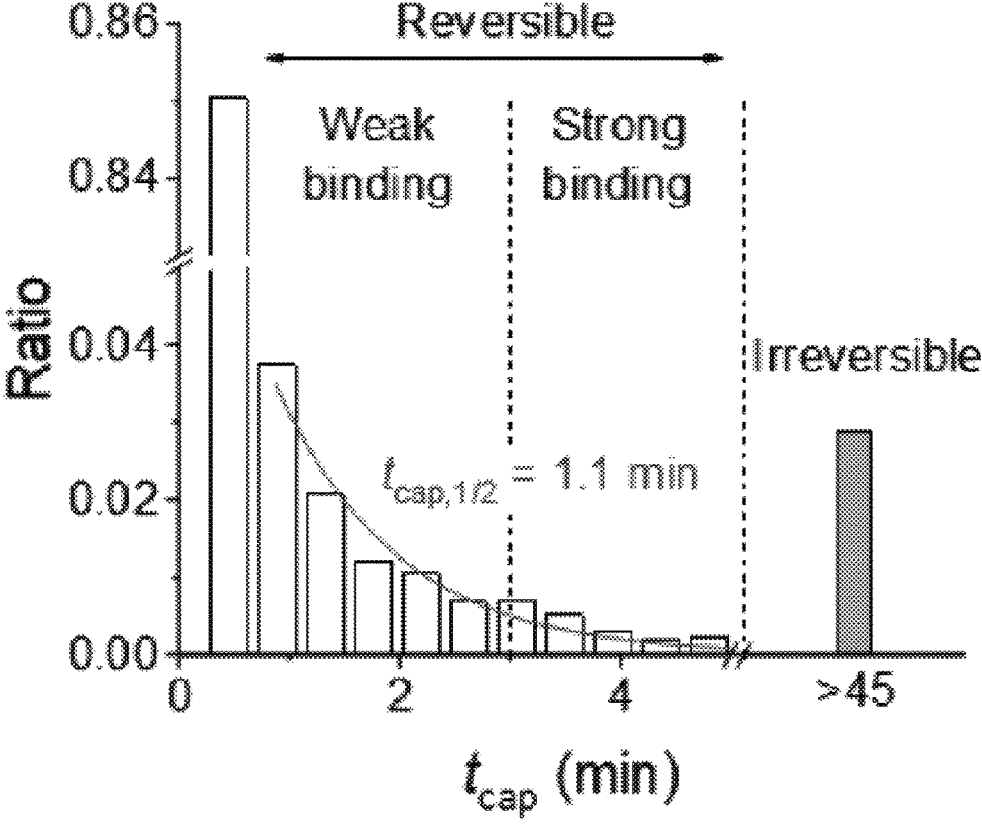
Figure 6G:
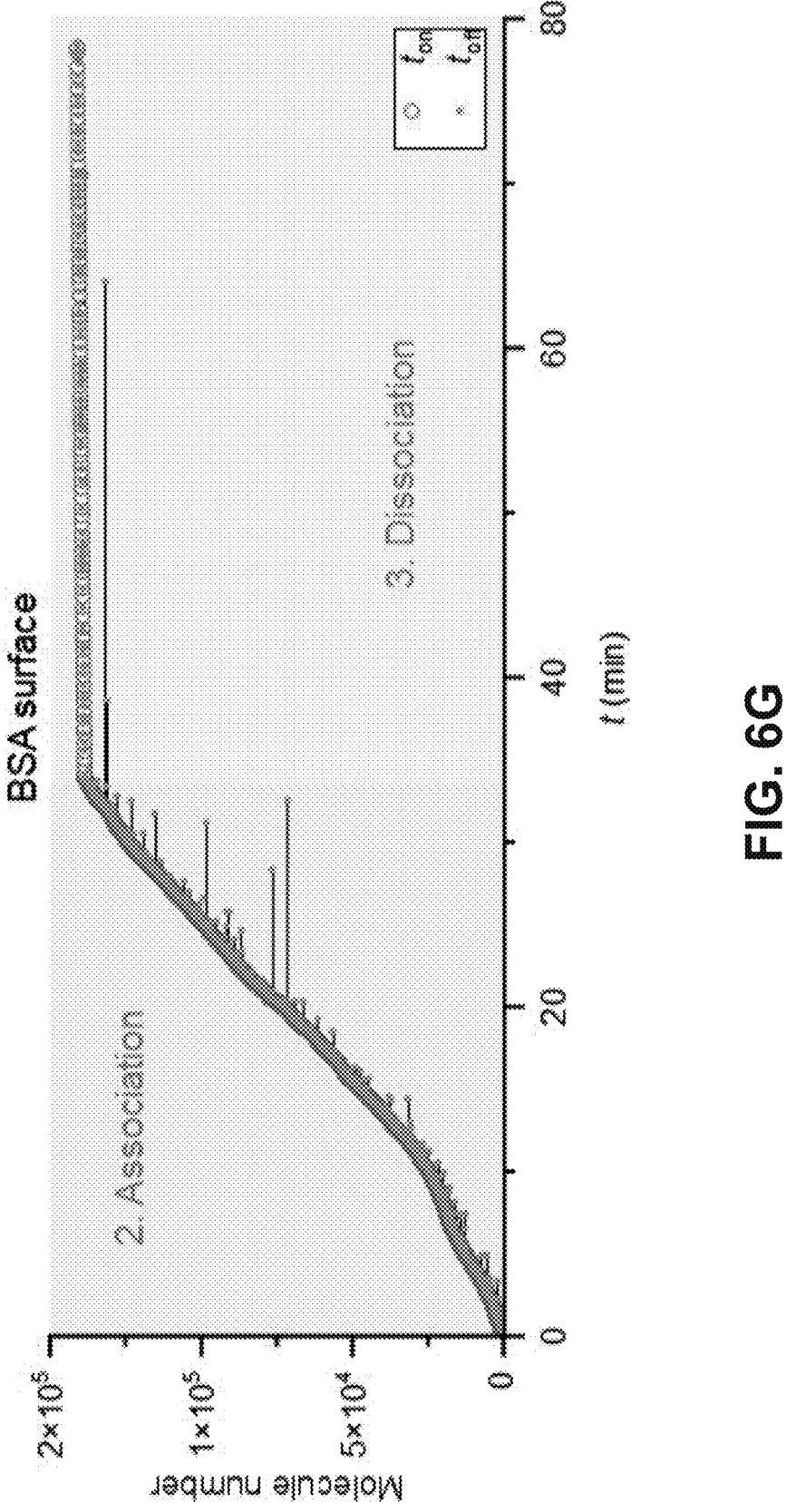
Figure 6H:
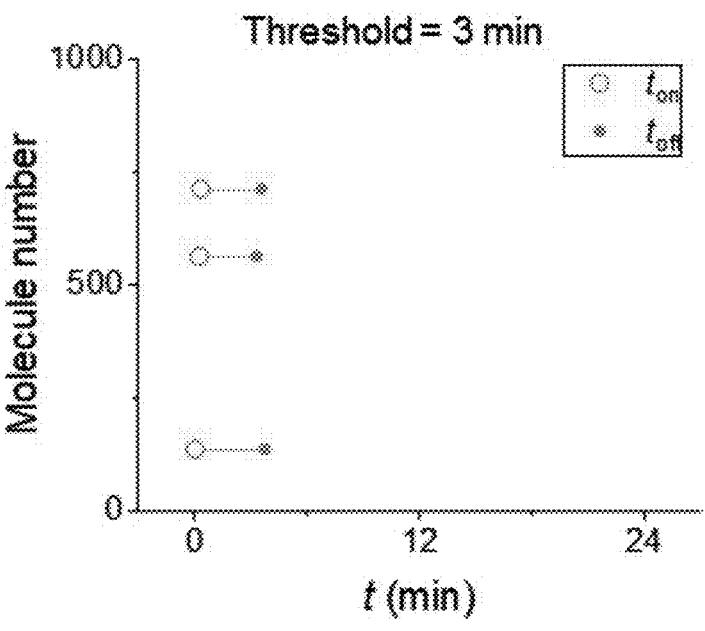
Figure 6I:
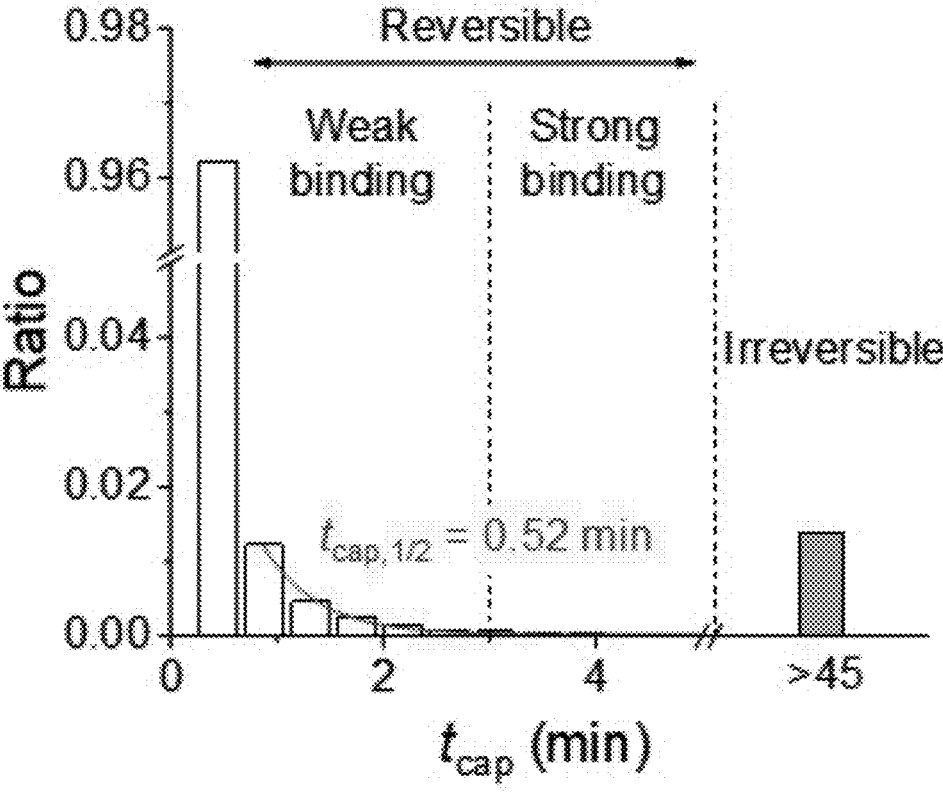

FIG. 6D shows the binding kinetics in FIG. 6B after we assigned all the binding and unbinding events to the single molecules (a zoom-in is shown in FIG. 6F for clarity). The timestamps for binding ($t_{on}$) and unbinding ($t_{off}$) are linked with a line, and the length $t_{cap}=t_{on}-t_{off}$ represents the capture time. As can be seen, most molecules only stayed on the surface for a short time, so the $t_{on}$ and $t_{off}$ are almost overlapped. By plotting the histogram of $t_{cap}$, we obtained the lifetime distribution of binding events (FIG. 6E), with a half-life fitted to be 1.1 min. Note that only molecules with both $t_{on}$ and $t_{off}$ identified are included in the histogram. Those only have $t_{on}$ but did not come off after the dissociation process are plotted separately aside the histogram (grey bar). These molecules are the same ones left at the end of dissociation in FIG. 6C, which are likely attached to the surface irreversibly. Accordingly, we categorize the binding events into reversible binding and irreversible binding. We note that all signals ($R_{cap}$) shown in the above sections are obtained using the irreversibly bound molecules, which contain massive nonspecific components. A reasonable way to filter out the irreversible nonspecific binding signal would be to examine the data in the reversible binding domain. To test our hypothesis, we performed a control experiment using a BSA coated surface, which only contributed to nonspecific signals (FIGS. 6G and 6I). The histogram of $t_{cap}$ indeed showed a smaller binding half-time of 0.52 min (FIG. 6H) compared to that of the anti-mTOR surface, indicating weaker interactions. We also measured a PEG2k coated surface, which has similar nonspecific binding level as BSA. These results confirm the validity of using the reversible domain to improve detection specificity.

Figure 6J:
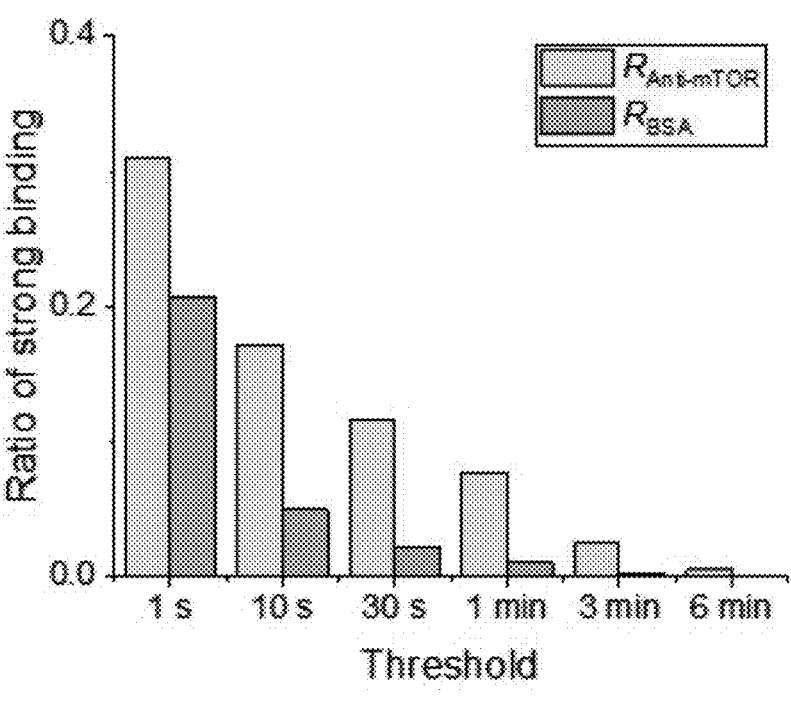
Figure 6K:
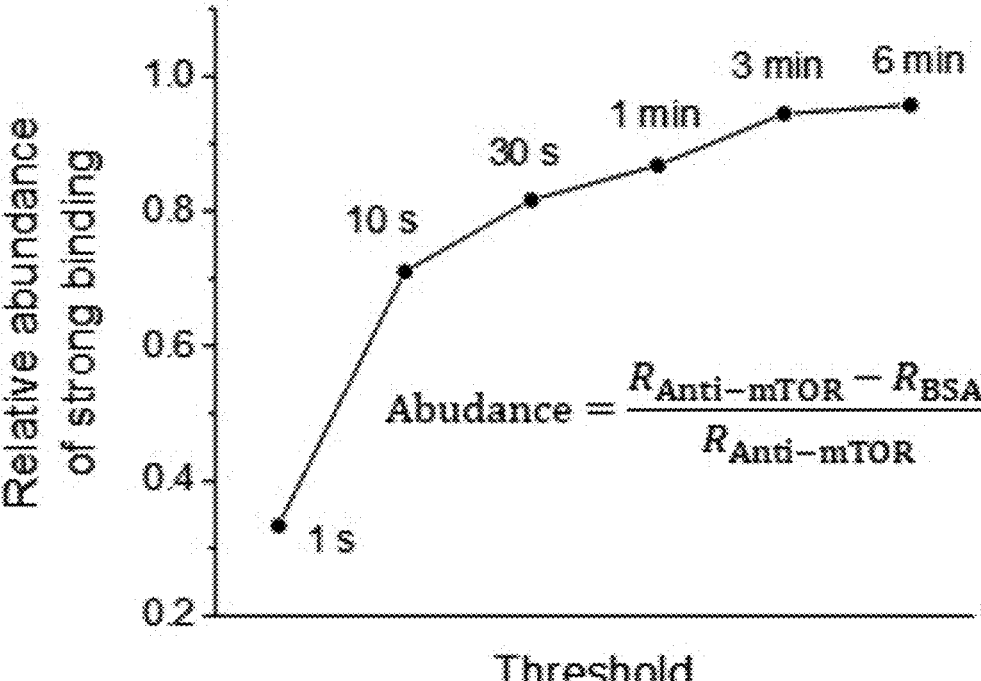
Figure 6L:
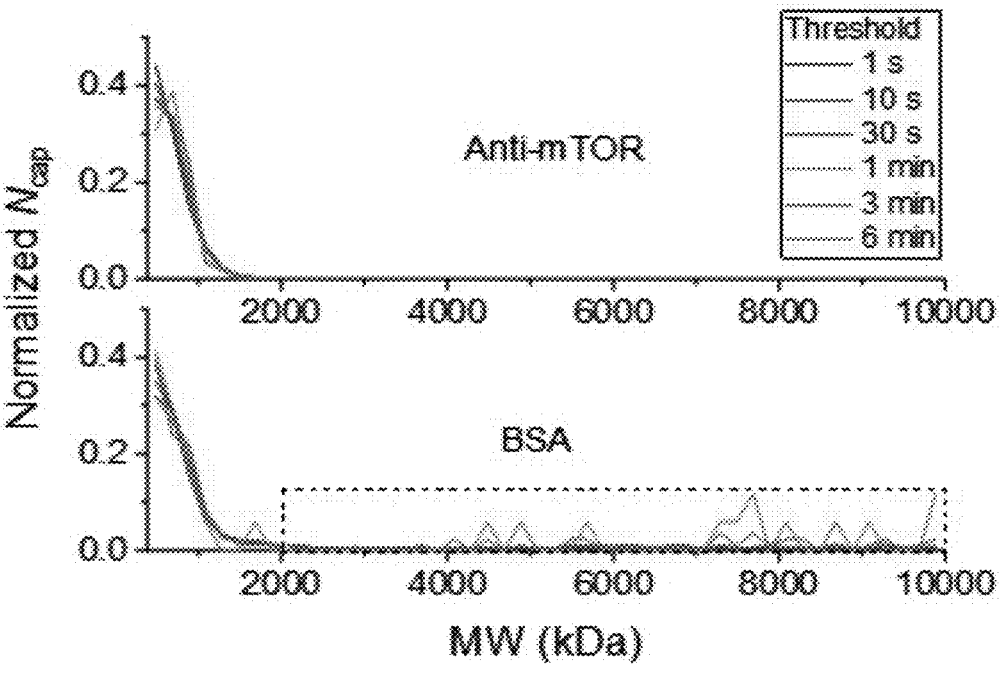
Figure 6M:
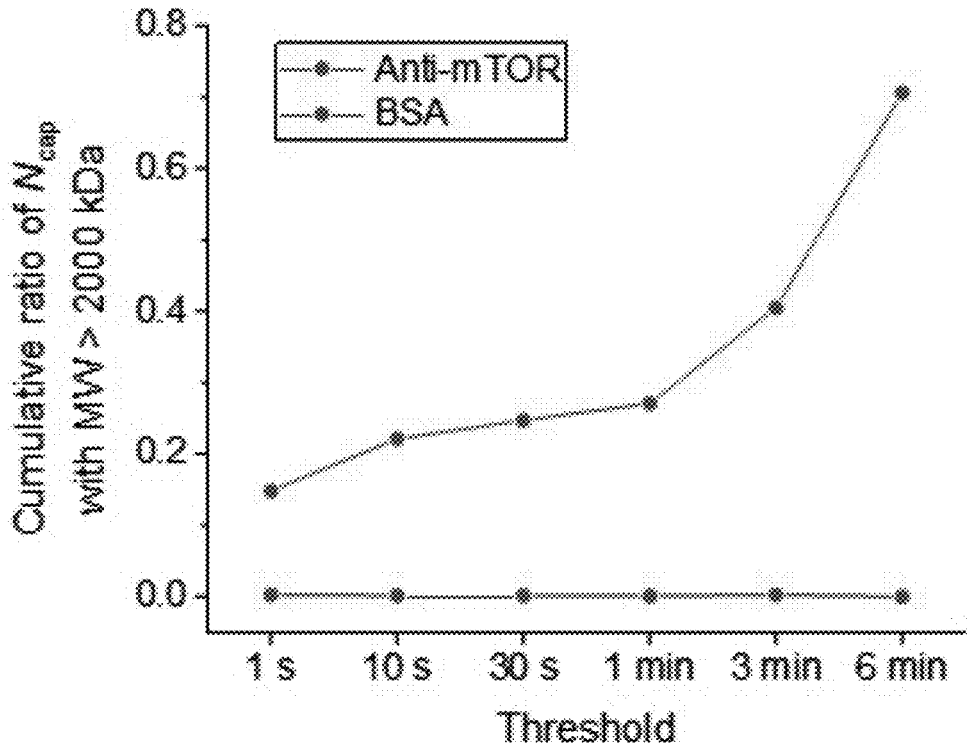

Not all the interactions in reversible domain are specific. The next task is to quantify the specific component within the reversible domain. $t_{cap}$ ranges from zero to several minutes, and the short $t_{cap}$ is from unbound or weakly bound molecules, which is unlikely caused by the strong specific binding between antibody and protein. Thus, the short $t_{cap}$ should be rejected. To find out the connection between $t_{cap}$ and specific binding, we first arbitrarily set a threshold to $t_{cap}$ at 3 min, which separates $t_{cap}$ into a weak binding region and a strong binding region (FIGS. 6E and 6H). After rejecting the weak binding having $t_{cap}$<3 min, the remaining strong binding is plotted in FIGS. 6F and 6I (only the strong binding in the first 1000 imaged molecules are shown as an example). The anti-mTOR surface showed more bound molecules than the BSA surface, which is as expected. Next, we scanned the threshold from 1 s to 6 min and calculated the cumulative ratio of strong binding events for both anti-mTOR ($R_{Anti-mTOR}$) and BSA surfaces ($R_{BSA}$) (FIG. 6J). The relative difference between $R_{Anti-mTOR}$ and $R_{BSA}$, defined by ($R_{Anti-mTOR}$–$R_{BSA}$)/$R_{Anti-mTOR}$, is a measure of the abundance of specific binding, which increases with the threshold and approaches ~1 at threshold=6 min (FIG. 6K). This suggests almost all interactions are specific at high $t_{cap}$. We also examined the MW of the filtered molecules. The MW distribution at different thresholds is plotted in FIG. 6I. The distribution profile for anti-mTOR and BSA surfaces are close except the high MW region at MW>2000 kDa. The BSA surface has a higher level of high MW molecules than the anti-mTOR surface, which indicates heavier molecules are more prone to nonspecific interactions. By integrating the high MW region in FIG. 6L (dashed square), we also found that the total ratio of high MW molecules on BSA surface increases with the threshold value (FIG. 6M). In contrast, the anti-mTOR surface does not have such high MW bindings. Together, our results show the feasibility of using capture time to refine specific binding signals and larger molecules are more likely to cause nonspecific binding in complex media (such as cell lysate).

Discussion

Mass Detection Accuracy is Compromised for Unbound Molecules

In PSM, the MW is determined by the number of scattered photons by molecules within the evanescent field. Considering the exponential decay of the field, the same molecule scatters less photons when it is away from the surface. Same issue applies for a molecule that does not stay in the field for enough time. Consequently, the measured MW shows a wide distribution. This peak broadening effect can be mitigated by functionalizing the surface with antibody to capture the molecule. Although this strategy has been used in our previous PSM studies for pure sample measurements, it is not applicable for measuring multiple types of proteins simultaneously in a mixture, such as cell lysate. This is simply because one cannot modify thousands of different antibodies to the surface at the same time, not to mention if they are available. Yet, the specific pulldown of one complex from lysate should report accurate MW. The calibration curve in FIG. 3C was obtained without using antibodies, thus the standard deviation (s.d.) reflects the accuracy of mass measurement in mixture, and the coefficient of variation (CV) is found to be 38.5%. As a comparison, the CV is about 19.1% for the same measurements with antibody.

Actual Hitting Rate, Effective Hitting Rate and Imaging Efficiency

The collision process of an unbound molecule to the surface includes a hitting event and a leaving event, which generates a bright spot and a dark spot on PSM image, respectively (FIG. 4B). If the collision takes place faster than the camera frame rate, the molecule will not be imaged because the bright spot and the dark spots "cancel out". Therefore, for a mixture sample with various unbound molecules, the recorded images only show a portion of the hitting molecules. Next, we attempt to find a connection between them. Theoretically, the particle collision frequency or the actually hitting rate, f, can be calculated using f≈4Drc, where D is the diffusion coefficient of protein ($5\times10^{-11}$ $m^2/s$),[35] r is the radius of the imaging area (~6 μm), and c is the protein concentration. The number of hitting events recorded by PSM (or effective hitting rate) is found to be proportional to the sample concentration, given by $f_{eff}$=kc, as determined by measuring different concentrations of IgM. Thus, the hitting event imaging efficiency is $E=f_{eff}/f=4.0\times10^{-5}$. This number implies that the collision of most unbound molecules is not recorded. For bound molecules, however, they do not leave the surface after hitting, so all the hitting events should be recorded.

A Glance of the Intracellular Protein Complex Number

Using the hitting rate, we can estimate the total number of protein complexes in the cell. FIG. 3H shows the hitting rate at 1 cell/$10^4$ μm$^2$ density is about $f_{eff}$=1000 hits/min, which is 590 nM in concentration. Using $10^4$ μm$^2$ as the surface area and 51 μm as channel height, the total number of molecules released by the single cell is $1.8\times10^8$. Note that this number measured by PSM represents large complexes with MW>385 kDa, but not the total number of intracellular proteins. According to an estimation by Milo, the total number of proteins in a HeLa cell is about $1\times10^{10}$. Thus, our result implies that the number of large complex molecules constitutes ~2% of the total protein in HeLa cell.

Design for Single-Molecule Single-Cell Detection

Understanding the heterogeneity in single cells is one of the fundamental tasks in cell biology. LFSMP can achieves single cell resolution with single-molecule sensitivity. The bright field and the PSM is used to locate a single cell and image the single molecules under the cell simultaneously.

However, to measure a single cell accurately, the cell should be well-isolated from the neighboring ones to avoid cross-talk. By using microwell arrays, released molecules are trapped. An additional benefit of using microwells is that the small volume (e.g., 30×30×30 $\mu m^3$) concentrates the molecules and increases the hitting frequency. An adherent single cell in a microwell corresponds to 60% confluence, $f_{eff}=10^4$ hits/min that can be readily achieved (FIG. 3H).

Tradeoff Between Specificity and Detection Time

The real-time kinetic measurement permits excluding weak interactions and improving the binding specificity, but it takes longer time. As shown in FIG. 6J, counts decline dramatically with higher threshold. Although the 6 min threshold for anti-mTOR can keep >90% specific interactions (FIG. 6K), the remaining counts is only 0.55% of the total counts (FIG. 6J). Longer sampling time is needed to collect more counts, otherwise the data may suffer from digital counting noise. Protein complex disassembly in the lysis buffer is an additional concern for long term detection. A balance between detection time and specificity should be reached, which needs further investigation.

Conclusion

We have demonstrated LFSMP as a label-free intracellular protein analysis tool with single-molecule imaging capability. By functionalizing the surface with antibodies, protein complex of interest can be specifically pulled down from the cell lysate with minimal perturbation to the native composition, allowing signaling pathway studies and real-time binding kinetics analysis. The current design of LFSMP can measure as low as 25 cells/$mm^2$. We anticipate the integration with microfabrication techniques will develop LFSMP into a powerful single-molecule single-cell analysis platform.

Methods

Experimental setup. The incident light of PSM was an 80-mW laser (OBIS 660-75FP, Coherent) with central wavelength at 660 nm. The light was first conditioned by a lens group and then focused onto the back focal plane of a 100× objective. The focused Gaussian beam was then projected to the prism surface using another group of lenses with an incident angle of 71° for SPR excitation. The reflected light from the gold film was collected by a CMOS camera (CM3-U3-13Y3MCS, Point Grey) to assist finding the correct SPR angle. The scattered light from the gold film surface was collected by a 60× objective (Olympus, LUCPLFLN60X, NA=0.7) and imaged by another CMOS camera (MQ013MG-ON, XIMEA).

Materials. Human colostrum immunoglobulin A (IgA), human plasma immunoglobulin M (IgM), and human low-density lipoproteins (LDL) were purchased from Athens Research and Technology. Rabbit Raptor antibody and rabbit phospho-Raptor antibody were purchased from Cell Signaling Technology. DyLight 488 goat anti-rabbit IgG was purchased from MyBiosource. Mouse mTOR antibody was purchased from Invitrogen. Phosphate-buffered saline (PBS) was purchased from Corning. Bovine serum albumin (BSA), human thyroglobulin (Tg), 5-aminoimidazole-4-carboxamide (AICAR), poly-L-lysine, N-hydroxysulfosuccinimide sodium salt (NHS), N-(3-dimethylaminopropyl)-N'-ethyl-carbodiimide hydrochloride (EDC), and O-(2-Carboxy-ethyl)-O'-(2-mercaptoethyl)heptaethylene glycol (SH- PEG8-COOH) were purchased from Sigma-Aldrich. Methyl-PEG4-thiol (MT(PEG)$_4$) was purchased from Thermo Fisher Scientific. PEG2k was obtained from Nanocs. The materials and chemicals for SDS-PAGE were purchased from Bio-Rad if not stated specifically.

Cell culture. HeLa cells were obtained from the American Type Culture Collection. The cells were cultured in Dulbecco's modified eagle medium (DMEM; Lonza) in a humidified incubator at 37° C. with 5% $CO_2$. To active the phosphorylation of Raptor, the cells were cultured in either glucose-free DMEM for 24 hours or in normal DMEM with 1 mM AICAR for 1 hour before the experiment. All the DMEM were supplied with 10% fetal bovine serum (Invitrogen) and 1% penicillin and streptomycin (BioWhittaker). For PSM imaging, the cells were harvested at 75% confluence, diluted, and transferred to the surface of a pre-assembled, poly-L-lysine treated flow channel top piece.

Cell lysis and western blotting. Cells were removed from the flask using Trypsin-EDTA (25-300-054, Fisher Scientific) and suspended in PBS followed by incubating in ice-cold 1× lysis buffer (9803S, Cell Signaling Technology) with protease inhibitor (A32953, Thermo Scientific) for 10 min. The lysate was sonicated for 30 s, and then centrifuged for 10 min at 14,000×g at 4° C. The supernatant was collected, and the protein concentration was measured with BCA assay (23227, Thermo Fisher Scientific). The proteins were resolved by SDS-PAGE and transferred to PVDF membrane for western blotting. The detection signal was amplified by enhanced chemiluminescence (PI34580, Fisher Scientific).

Surface functionalization. The gold film was fabricated by coating No. 1 cover glass with 1.5 nm Cr and then 43 nm gold using an e-beam evaporator. After rinsing with ethanol and DI water each for three times, dried with $N_2$, and annealed with $H_2$ flame, the gold film was soaked in a solution containing 0.2 mM SH-PEG8-COOH and 0.2 mM MT(PEG)$_4$ overnight. Then the COOH groups were activated by incubating the film with 50 mM NHS and 200 mM EDC for 20 min. Next, 300 nM antibody in PBS was immediately added to the gold surface and incubated for 1 hour to allow immobilization of the protein. Note that prior to protein immobilization, the buffer was transferred to PBS using Zeba desalting columns (Thermo Scientific) if the original buffer was not pure PBS. 20 mM ethanolamine was used to quench the remaining active sites for 10 min. Finally, the functionalized gold film was blocked with 0.1% BSA for 10 min. The BSA blocked chips were made by incubating the NHS/EDC activated surface with 0.1% BSA for 1 hour. The PEG2k blocked chips were fabricated by incubating clean gold film in 100 µM PEG2k overnight.

Flow channel assembly. The flow channel consists of three parts: an antibody-functionalized gold film on the bottom, a cover glass on the top, and a spacer in between. The top cover glass (No. 1, 18×18 mm) was drilled with two holes (diameter, 1 mm) which served as the inlet and the outlet. Plastic tubing (AAD04103, TYGON) was connected to the holes via a small PDMS block. The flow channel spacer was made by laser-cutting a 51-µm thick double-sided tape (9628B, 3M), which sticked the top and bottom pieces together.

Image processing. The image sequence was recorded using XIMEA CamTool and processed using Fiji. After recording the raw image sequence, a differential image sequence was obtained by subtracting the previous frame from each frame. Common background was removed in the differential images and single molecule spots were revealed. After smoothing the images with the smooth function in Fiji, the single molecule spots were counted and the intensity was measured using TrackMate, a plugin integrated in Fiji.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of detecting unlabeled biomolecules, the method comprising:
a fluidic device, comprising a body structure that defines at least one chamber disposed substantially within the body structure, wherein the chamber comprises a fluidic material and at least first and second inner surfaces, wherein a cell population is disposed on the first inner surface, and wherein the second inner surface is coated with a metallic layer that is configured to create surface plasmon resonance when incident light is introduced toward the second inner surface at a suitable incident angle via a second outer surface of the chamber;
lysing at least one cell in the cell population sufficient to release at least some unlabeled biomolecules from the at least one cell in the cell population to produce released biomolecules;
binding at least a portion of the released biomolecules to a second inner surface of the chamber to produce one or more surface-bound biomolecules;
introducing an incident light toward the second inner surface of the chamber concurrent with, and/or after, producing the surface-bound biomolecules; and,
detecting light scattered by the surface-bound biomolecules over a first duration to produce a set of biomolecule imaging data, thereby detecting the unlabeled biomolecules.

2. The method of claim 1, further comprising culturing the cell population on the first inner surface of the chamber prior to performing the lysing step.

3. The method of claim 1, comprising performing the lysing, binding, introducing, and detecting steps substantially simultaneously with one another.

4. The method of claim 1, comprising detecting the light scattered by the surface-bound biomolecules in substantially real-time.

5. The method of claim 1, further comprising determining a molecular weight of at least one of the unlabeled biomolecules using the set of biomolecule imaging data.

6. The method of claim 1, further comprising determining a composition of at least one of the unlabeled biomolecules using the set of biomolecule imaging data.

7. The method of claim 1, further comprising quantifying the unlabeled biomolecules and/or binding kinetics thereof using the set of biomolecule imaging data.

8. The method of claim 1, comprising introducing the incident light toward the second inner surface via a second outer surface of the chamber.

9. The method of claim 1, wherein the set of biomolecule imaging data comprises video data.

10. The method of claim 1, wherein the fluidic device comprises at least one inlet port and at least one outlet port that both fluidly communicate with the chamber and wherein the method further comprises flowing the fluidic material into the chamber via the inlet port and out of the chamber via outlet port.

11. The method of claim 10, wherein the fluidic material comprises a ligand that binds to the surface-bound biomolecules to produce one or more surface-bound ligand-biomolecule complexes and wherein the method further comprises detecting light scattered by the surface-bound ligand-biomolecule complexes over a second duration to produce a set of ligand-biomolecule complex imaging data.

12. The method of claim 11, further comprising detecting size or volume changes of the surface-bound ligand-biomolecule complexes during at least a portion of the second duration from the set of ligand-biomolecule complex imaging data to thereby determine a molecular binding kinetics measure of the unlabeled biomolecules.

13. The method of claim 1, wherein the second surface of the chamber comprises a plurality of biomolecule capture moieties that are capable of binding the released biomolecules and wherein the method comprises binding the released biomolecules to the second surface of the chamber via at least a portion of the plurality of biomolecule capture moieties to produce the one or more surface-bound biomolecules.

14. The method of claim 1, wherein the second inner surface is coated with a metallic layer and wherein an incident angle of the incident light is selected to create surface plasmon resonance on the metallic layer.

15. The method of claim 1, wherein a roughness of the second inner surface is selected such that light scattered by the second inner surface interferes with at least some of the light scattered by the surface-bound biomolecules.

16. The method of claim 1, further comprising counting a number of individual surface-bound biomolecules over the first duration to produce a count and fitting the count with a binding model to determine kinetic constants and/or at least one affinity value.

17. A fluidic device, comprising a body structure that defines at least one chamber disposed substantially within the body structure, wherein the chamber comprises a fluidic material and at least first and second inner surfaces, wherein a cell population is disposed on the first inner surface, and wherein the second inner surface is coated with a metallic layer that is configured to create surface plasmon resonance when incident light is introduced toward the second inner surface at a suitable incident angle via a second outer surface of the chamber.

18. The fluidic device of claim 17, wherein the second surface comprises a plurality of biomolecule capture moieties that are capable of binding unlabeled biomolecules when the unlabeled biomolecules are released from at least one cell in the cell population.

19. A system for detecting unlabeled biomolecules, comprising:

a fluidic device receiving area configured to receive a fluidic device that comprises a body structure that defines at least one chamber disposed substantially within the body structure, wherein the chamber comprises a fluidic material and at least first and second inner surfaces, wherein a cell population is disposed on the first inner surface, and wherein the second inner surface is coated with a metallic layer that is configured to create surface plasmon resonance when incident light is introduced toward the second inner surface at a suitable incident angle via a second outer surface of the chamber;

a light source configured to introduce an incident light toward the fluidic device receiving area;

a detector configured to collect light scattered by surface-bound biomolecules when the fluidic device is received in the fluidic device receiving area and the incident light is introduced from the light source; and a controller that comprises, or is capable of accessing, computer readable media comprising non-transitory computer-executable instructions which, when executed by at least one electronic processor, perform at least:

lysing at least one cell in the cell population sufficient to release at least some unlabeled biomolecules from the at least one cell in the cell population to produce released biomolecules such that at least a portion of the released biomolecules bind to the second inner surface of the chamber to produce one or more surface-bound biomolecules when the fluidic device is received in the fluidic device receiving area;

introducing the incident light from the light source at the suitable incident angle toward the second inner surface of the chamber when the fluidic device is received in the fluidic device receiving area; and, detecting light scattered by the surface-bound biomolecules over a duration to produce a set of biomolecule imaging data to thereby detect the unlabeled biomolecules using the detector when the fluidic device is received in the fluidic device receiving area.

20. The system of claim 19, wherein the set of biomolecule imaging data comprises video data.

21. The system of claim 19, wherein the non-transitory computer-executable instructions which, when executed by the electronic processor, further perform at least: determining a molecular weight of at least one of the unlabeled biomolecules using the set of biomolecule imaging data.

22. The system of claim 19, wherein the non-transitory computer-executable instructions which, when executed by the electronic processor, further perform at least: determining a composition of at least one of the unlabeled biomolecules using the set of biomolecule imaging data.

23. The system of claim 19, wherein the non-transitory computer-executable instructions which, when executed by the electronic processor, further perform at least: quantifying the unlabeled biomolecules and/or binding kinetics thereof using the set of biomolecule imaging data.

24. The system of claim 19, wherein the non-transitory computer-executable instructions which, when executed by the electronic processor, perform at least: lysing at least one cell in the cell population using at least one laser.

25. The system of claim 19, wherein the fluidic device comprises at least one inlet port and at least one outlet port that both fluidly communicate with the chamber and wherein the non-transitory computer-executable instructions which, when executed by the electronic processor, further perform at least: flowing the fluidic material into the chamber via the inlet port and out of the chamber via outlet port using at least one fluid conveyance device.

26. The system of claim 19, wherein the second surface of the chamber comprises a plurality of biomolecule capture moieties that bind the released biomolecules to produce the one or more surface-bound biomolecules.

\* \* \* \* \*